(12) United States Patent
Akagane

(10) Patent No.: US 9,464,961 B2
(45) Date of Patent: Oct. 11, 2016

(54) INSPECTION PROBE, VIBRATION STATE INSPECTION SYSTEM, AND METHOD OF INSPECTING VIBRATION STATE

(71) Applicant: OLYMPUS CORPORATION, Hachioji-shi, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/073,053

(22) Filed: Mar. 17, 2016

(65) Prior Publication Data
US 2016/0195450 A1    Jul. 7, 2016

Related U.S. Application Data

(63) Continuation of application No. PCT/JP2014/083017, filed on Dec. 12, 2014.

(30) Foreign Application Priority Data

Dec. 13, 2013  (JP) ................................ 2013-258521

(51) Int. Cl.
*A61B 18/00* (2006.01)
*H04R 17/00* (2006.01)
(Continued)

(52) U.S. Cl.
CPC ................ *G01M 7/022* (2013.01); *G01K 7/02* (2013.01)

(58) Field of Classification Search
CPC ................. A61B 17/320092; A61B 18/1445; A61B 2017/00026; A61B 2017/00106
USPC ........................................................ 73/618
See application file for complete search history.

(56) References Cited

U.S. PATENT DOCUMENTS

| 6,730,048 B1* | 5/2004 | Hare | A61B 17/22012 601/2 |
| 8,740,835 B2* | 6/2014 | Soltani | A61K 9/0009 604/22 |
| 8,790,359 B2* | 7/2014 | Rabiner | A61B 17/22012 606/169 |

(Continued)

FOREIGN PATENT DOCUMENTS

| JP | 2003-000610 A | 1/2003 |
| JP | 2003-159259 A | 6/2003 |

(Continued)

OTHER PUBLICATIONS

Aug. 18, 2015 Office Action issued in Japanese Patent Application No. 2015-528761.

(Continued)

*Primary Examiner* — J M Saint Surin
(74) *Attorney, Agent, or Firm* — Oliff PLC

(57) ABSTRACT

An inspection probe includes a vibration transmission portion transmitting an ultrasonic vibration along a longitudinal axis, and a vibration damping portion continuous with a distal direction side of the vibration transmission portion. the vibration damping portion damps the ultrasonic vibration by causing vibration energy of the ultrasonic vibration to be lost and converting the lost vibration energy to heat energy in a state that the vibration damping portion vibrates in a manner to follow the vibration transmission portion. An index section of the inspection probe serves as an index indicating a conversion amount to the heat energy in the vibration damping portion.

14 Claims, 11 Drawing Sheets

(51) Int. Cl.
*G01M 7/02* (2006.01)
*G01K 7/02* (2006.01)

(56) References Cited

U.S. PATENT DOCUMENTS

| | | |
|---|---|---|
| 2002/0049427 A1 | 4/2002 | Wiener et al. |
| 2002/0049551 A1 | 4/2002 | Friedman et al. |
| 2009/0259149 A1 | 10/2009 | Tahara et al. |
| 2009/0259243 A1 | 10/2009 | Tahara et al. |

FOREIGN PATENT DOCUMENTS

| | | | |
|---|---|---|---|
| JP | 2006-511269 A | | 4/2006 |
| JP | 2007-159737 A | | 6/2007 |
| JP | 2009-254819 A | | 11/2009 |
| JP | 2009-254820 A | | 11/2009 |
| JP | 2009-254821 A | | 11/2009 |
| JP | 2013-106635 A | | 6/2013 |
| JP | 2013242202 | * | 12/2013 |
| WO | 2004/058074 A1 | | 7/2004 |

OTHER PUBLICATIONS

Jan. 27, 2015 Search Report issued in International Patent Application No. PCT/JP2014/083017.

* cited by examiner

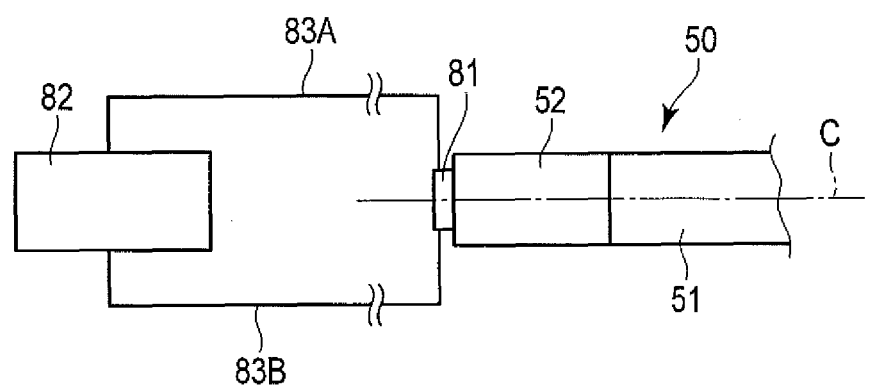
F I G. 11
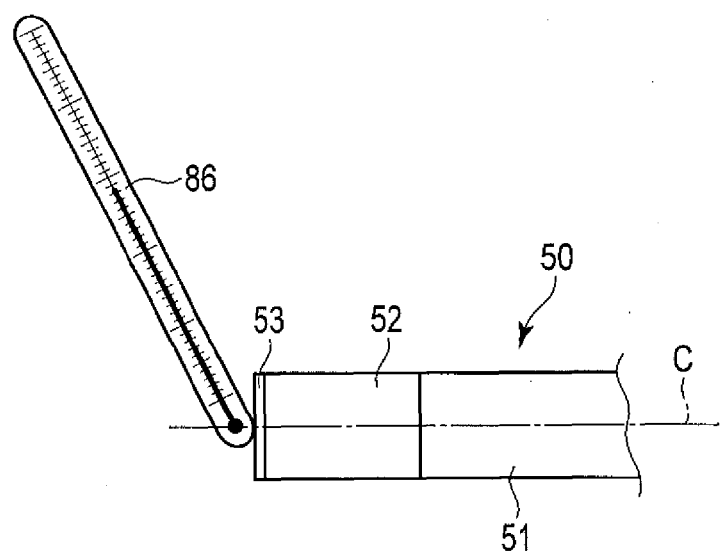
F I G. 12

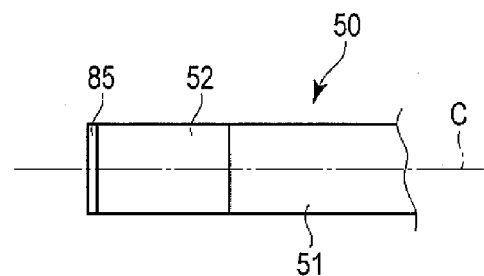
F I G. 13
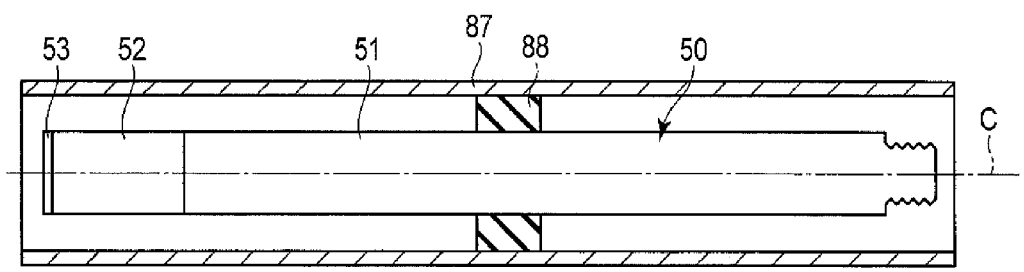
F I G. 14

INSPECTION PROBE, VIBRATION STATE INSPECTION SYSTEM, AND METHOD OF INSPECTING VIBRATION STATE

CROSS-REFERENCE TO RELATED APPLICATIONS

This is a Continuation application of PCT Application No. PCT/JP2014/083017, filed Dec. 12, 2014 and based upon and claiming the benefit of priority from prior Japanese Patent Application No. 2013-258521, filed Dec. 13, 2013, the entire contents of which are incorporated herein by reference.

BACKGROUND OF THE INVENTION

1. Field of the Invention

The present invention relates to an inspection probe for use in an inspection of a vibration state by an ultrasonic vibration, in an ultrasonic treatment apparatus which is configured to treat a treated target by using the ultrasonic vibration. In addition, the invention relates to a vibration state inspection system including the inspection probe, and a method of inspecting a vibration state using the vibration state inspection system.

2. Description of the Related Art

Jpn. Pat. Appln. KOKAI Publication No. 2009-254821 discloses an ultrasonic treatment apparatus which treats a treated target, such as a living body tissue, by using an ultrasonic vibration. In this ultrasonic treatment apparatus, an electric current is supplied from a current control unit to an ultrasonic transducer which is a vibration generator provided in a transducer unit, and thereby an ultrasonic vibration is generated. The generated ultrasonic vibration is transmitted from a proximal direction toward a distal direction in an ultrasonic probe which is provided in a handpiece that is an ultrasonic treatment instrument. In addition, using the transmitted ultrasonic vibration, treatment is performed at a treatment section provided in a distal portion of the ultrasonic probe. Besides, in this ultrasonic treatment apparatus, the temperature of the ultrasonic transducer is detected by an abnormality detection circuit which is provided in the current control unit. When the temperature of the ultrasonic transducer is higher than a threshold, an abnormal state in which the handpiece is not normally actuated, such as a state in which a crack occurs in the ultrasonic probe, is determined. Specifically, based on a determination result in the abnormality detection circuit, it is discriminated whether the handpiece including the ultrasonic probe is normally actuated or not.

BRIEF SUMMARY OF THE INVENTION

According to one aspect of the invention, an inspection probe includes that: a vibration transmission portion extends along a longitudinal axis, and configured to transmit an ultrasonic vibration from a proximal direction toward a distal direction; a vibration damping portion continuous with a distal direction side of the vibration transmission portion, and configured to damp the ultrasonic vibration by causing vibration energy of the ultrasonic vibration to be lost and converting the lost vibration energy to heat energy in a state in which the vibration damping portion vibrates in a manner to follow the vibration transmission portion by the transmission of the ultrasonic vibration from the vibration transmission portion; and an index section to which heat produced by the conversion of the vibration energy to the heat energy in the vibration damping portion is transferred, the index section serving as an index indicating a conversion amount to the heat energy in the vibration damping portion.

According to one another aspect of the invention, a method of inspecting a vibration state, including: supplying an inspection current from a current supply section of a current control unit to a vibration generator of a transducer unit; generating an ultrasonic vibration in the vibration generator by the supplied inspection current; transmitting the generated ultrasonic vibration from a proximal direction toward a distal direction in a vibration transmission portion provided in an inspection probe which is coupled to a distal direction side of the transducer unit; causing vibration energy of the ultrasonic vibration to be lost, and damping the ultrasonic vibration, by transmitting the ultrasonic vibration to a vibration damping portion which is continuous with the distal direction side of the vibration transmission portion, and causing the vibration damping portion to vibrate in a manner to follow the vibration transmission portion; converting the lost vibration energy to heat energy in the vibration damping portion, and producing heat; transferring the heat, which is produced in the vibration damping portion, to an index section serving as an index indicating a conversion amount to the heat energy in the vibration damping portion, and detecting a variation of the index section to which the heat is transferred; and making, based on a relationship between the inspection current, which is supplied from the current supply section, and the variation of the index section in a normal state in which the transducer unit and the current control unit are normally actuated, and based on a detection result of the variation of the index section, a discrimination of the normal state or otherwise.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 11 is a schematic view illustrating a state in which an electrical resistance value of a thermocouple according to a first modification is measured.

FIG. 12 is a schematic view illustrating a state in which the temperature of a heat radiation section according to a second modification is measured.

FIG. 13 is a schematic view illustrating the structure of an inspection probe according to a third modification.

FIG. 14 is a cross-sectional view which schematically illustrates the structures of an inspection probe and a cover member according to a fourth modification.

DETAILED DESCRIPTION OF THE INVENTION

First Embodiment

Figure 1:
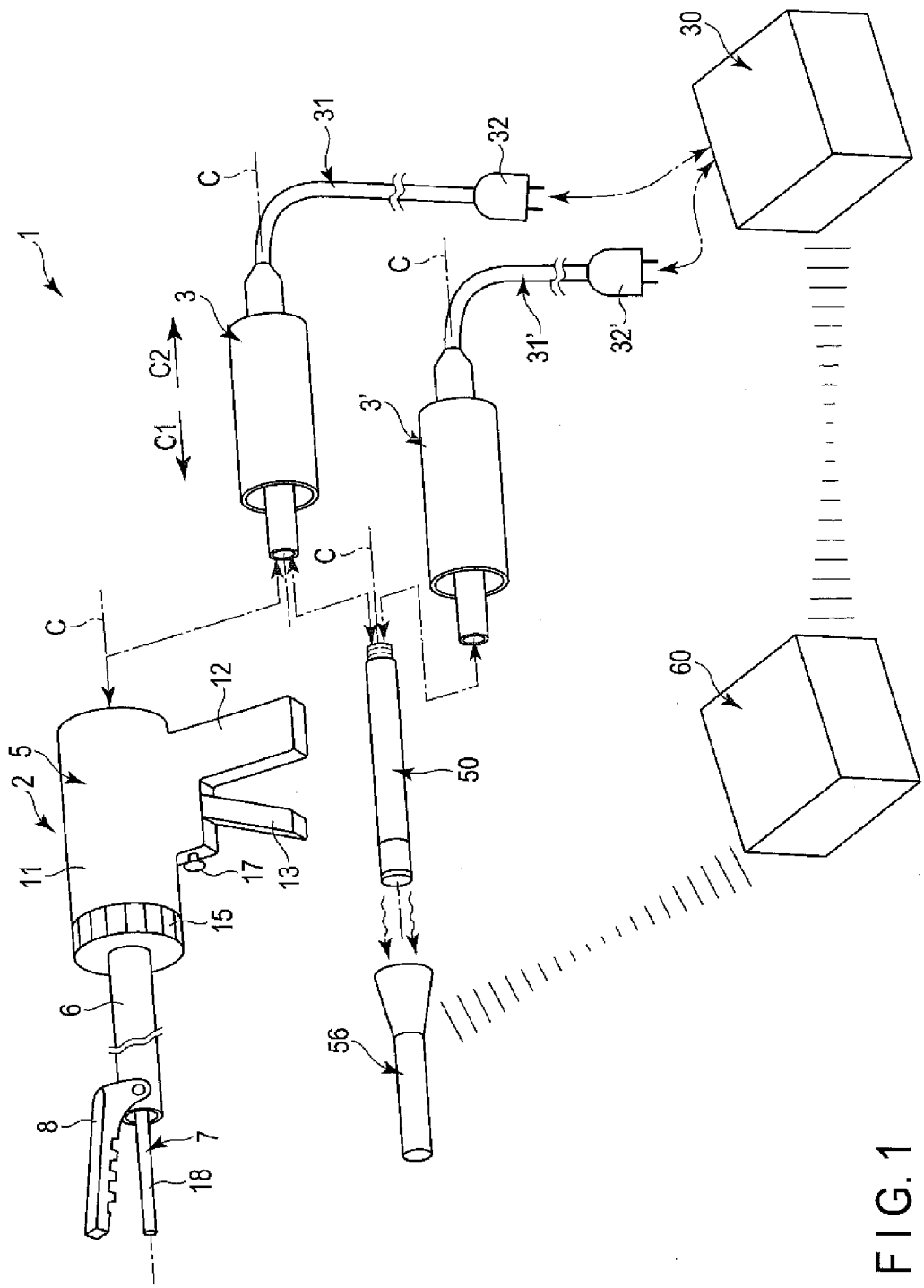
FIG. 1 is a perspective view which schematically illustrates a vibration state inspection system according to a first embodiment of the present invention.

A first embodiment of the present invention will be described with reference to FIG. 1 to FIG. 8. In this embodiment, a description is given of a vibration state inspection system 1 which is configured to inspect a vibration state by an ultrasonic vibration in a handpiece 2 that is an ultrasonic treatment instrument. FIG. 1 is a view illustrating the vibration state inspection system 1. As illustrated in FIG. 1, the vibration state inspection system 1 includes a transducer unit 3. The transducer unit 3 has a longitudinal axis C. Here, it is assumed that one of directions parallel to the longitudinal axis C is a distal direction (direction of arrow C1 in FIG. 1), and the direction opposite to the distal direction is a proximal direction (direction of arrow C2 in FIG. 1). Additionally, the distal direction and proximal direction are referred to as an axis-parallel direction.

At a time of treatment for treating a living body tissue or the like by using an ultrasonic vibration, the vibrator unit 3 is coupled to the handpiece 2 from the proximal direction side. Specifically, the transducer unit 3 is detachably coupled to the proximal direction side of the handpiece 2. The handpiece 2 includes a holding unit 5, a sheath 6, an ultrasonic probe 7, and a jaw 8. The holding unit 5 includes a cylindrical case portion 11 which extends along the longitudinal axis C, a stationary handle 12 which is provided as one piece with the cylindrical case portion 11, a movable handle 13 which is provided openable and closable relative to the stationary handle 12, and a rotary, operation knob 15 which is coupled to the distal direction side of the cylindrical case portion 11 in a state in which the rotary operation knob 15 is rotatable about the longitudinal axis C relative to the cylindrical case portion 11. The sheath 6 extends along the longitudinal axis C toward the distal direction, from the inside of the cylindrical case portion 11 through the inside of the rotary operation knob 16. In addition, the sheath 6 projects from the distal end of the holding unit 5 toward the distal direction. Specifically, the sheath 6 is coupled to the holding unit 5 in a state in which the sheath 6 is inserted, from the distal direction side, into the inside of the cylindrical case portion 11 through the inside of the rotary operation knob 15. In addition, a treatment energy operation button 17, which is a treatment energy operation portion, is attached to the stationary handle 12.

The ultrasonic probe 7 extends along the longitudinal axis C toward the distal direction, from the inside of the cylindrical case portion 11 through the inside of the rotary operation knob 16. A treatment section 18 is provided in a distal portion of the ultrasonic probe 7. The ultrasonic probe 7 is inserted through the sheath 6 in a state in which the treatment section 18 projects from the distal end of the sheath 6 toward the distal direction. The jaw 8 is rotatably attached to the distal portion of the sheath 6. By opening or closing the movable handle 13 relative to the stationary handle 12, a movable part (not shown) of the sheath 6 moves along the longitudinal axis C. Thereby, the jaw 8 rotates, and opens or closes relative to the treatment section 18 of the ultrasonic probe 7. In addition, by rotating the rotary operation knob 16 relative to the cylindrical case portion 11, the sheath 6, ultrasonic probe 7 and jaw 8 rotate, together with the rotary operation knob 16, about the longitudinal axis C relative to the cylindrical case portion 11.

Figure 2:
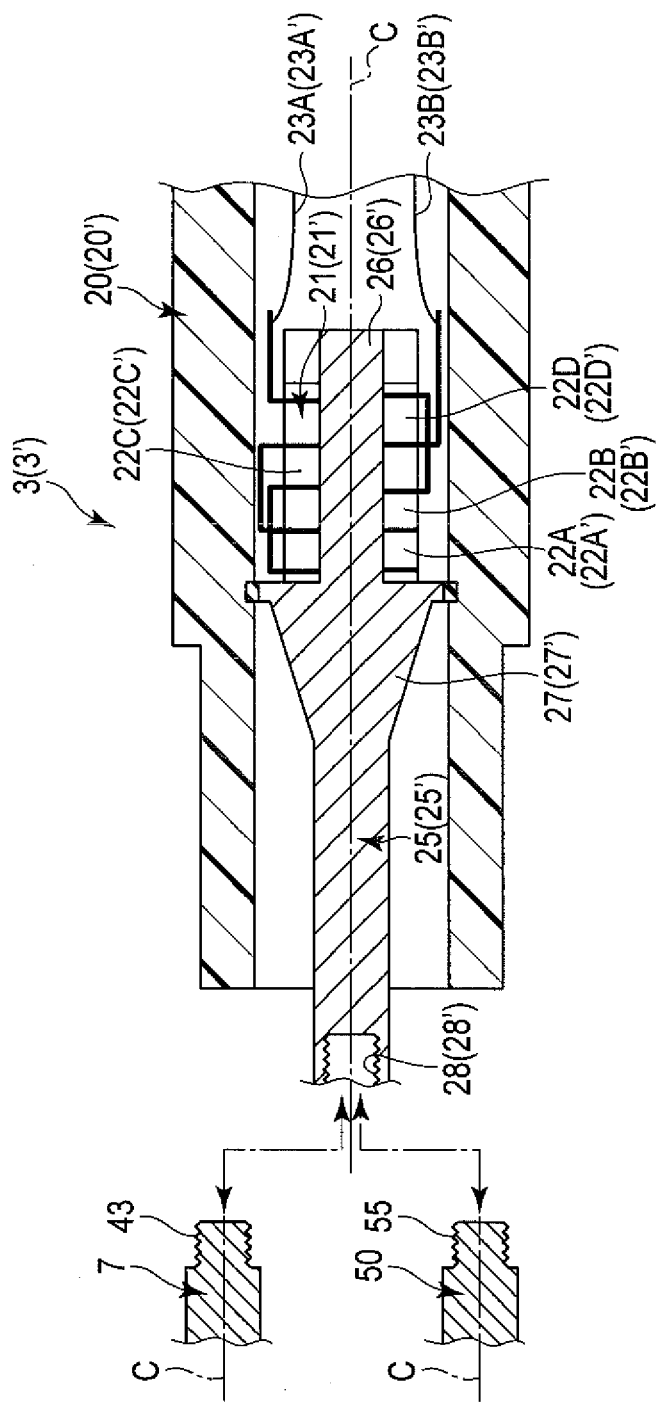
FIG. 2 is a cross-sectional view which schematically illustrates the structure of a transducer unit (inspection transducer unit) according to the first embodiment.

FIG. 2 is a view illustrating the structure of the transducer unit 3. As illustrated in FIG. 2, the transducer unit 3 includes a transducer case 20 and an ultrasonic transducer 21 which is a vibration generator accommodated inside the vibrator case 20. The ultrasonic vibrator 21 includes piezoelectric elements 22A to 22D (four in this embodiment) which are configured to convert an electric current to the ultrasonic vibration. The ultrasonic transducer 21 is supplied with an electric current, and thereby the ultrasonic vibration occurs in the ultrasonic vibrator 21. One end of an electric wiring line 23A, 233 is connected to the ultrasonic oscillator 21. In addition, the transducer unit 3 includes a columnar horn member 25 to which the ultrasonic transducer 21 is attached. The horn member 25 is attached to the transducer case 20 in a state in which the horn member 25 is situated within the transducer case 20. The horn member 25 includes a transducer attachment portion 26 to which the ultrasonic transducer 21 is attached, and a cross-sectional area varying portion 27 which is provided on the distal direction side with respect to the transducer attachment portion 26. In the cross-sectional area varying portion 27, the cross-sectional area perpendicular to the longitudinal axis C decreases from the proximal direction toward the distal direction. The amplitude of ultrasonic vibration is increased by the cross-sectional area varying portion 27. In addition, a female screw portion 28 is provided in a distal portion of the horn member 25.

As illustrated in FIG. 1, one end of a cable 31 is connected to the transducer unit 3. The other end of the cable 31 is provided with a cable connector 32. The cable connector 32 is detachably attached to a current control unit (energy source unit) 30. Specifically, the transducer unit 3 is detachably connected to the current control unit 30 via the cable 31. The handpiece 2 that is an ultrasonic treatment instrument, the transducer unit 3 and the current control unit 30 constitute an ultrasonic treatment apparatus 10 which is configured to treat a treated target, such as a living body tissue, by using the ultrasonic vibration. In the meantime, the current control unit 30 is, for example, an energy control device.

As illustrated in FIG. 2, a male screw portion 43 is formed in a proximal portion of the ultrasonic probe 7. The male screw portion 43 is engaged with the female screw portion 28 of the horn member 25, in the state in which the transducer unit 3 is coupled to the handpiece 2. Thereby, the ultrasonic probe 7 is connected to the distal direction side of the horn member 25 in the inside of the cylindrical case portion 11.

Figure 3:
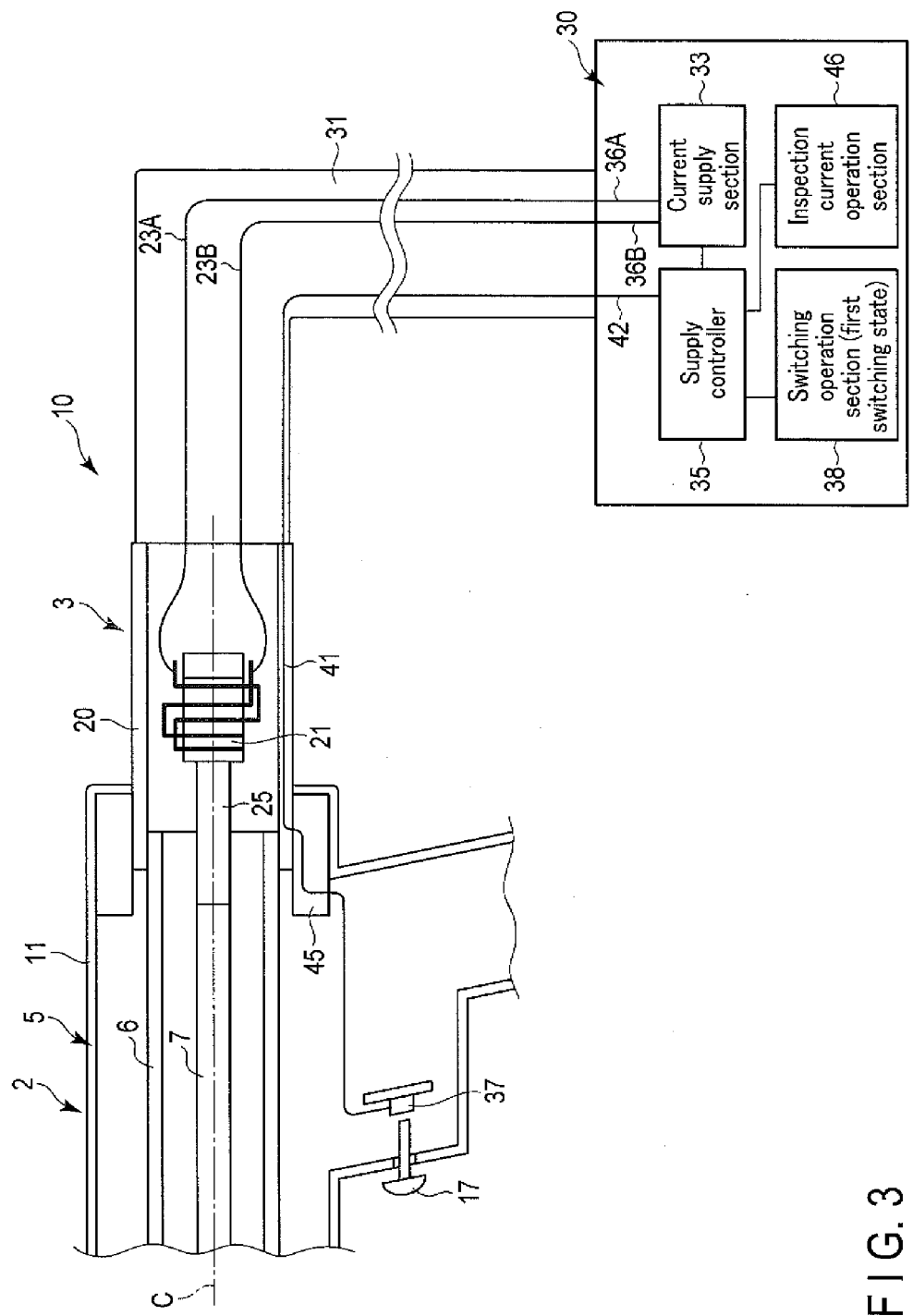
FIG. 3 is a schematic view illustrating an electrical connection state of an ultrasonic treatment apparatus according to the first embodiment.

FIG. 3 is a view illustrating an electrical connection state of the ultrasonic treatment apparatus 10. As illustrated in FIG. 3, at a time of treatment using the ultrasonic vibration, the transducer unit 3 is coupled to the handpiece 2, and the transducer unit 3 is connected to the current control unit 30 via the cable 31. In the state in which the transducer unit 3 is coupled to the handpiece 2, the transducer case 20 is attached to the cylindrical case 11 via an electrical connection ring 45. In addition, the electrical wiring lines 23A and 23B extend from the inside of the transducer case 20 through the inside of the cable 31. The current control unit 30 includes a current supply section 33, and a supply controller 35 which is configured to control the supply of current (electric power) from the current supply section 33. In addition, in the current control unit 30, there are provided unit-side electrical paths 36A and 36B which are connected at one end to the current supply section 33. By the cable connector 32 of the cable 31 being attached to the current control unit 30, the electrical wiring line 23A is electrically connected to the unit-side electrical path 36A, and the unit-side electrical path 36B is electrically connected to the electrical wiring line 23B. Thereby, the current supply section 33 and the ultrasonic transducer 21 are electrically connected via the electrical wiring lines 23A and 23B and the unit-side electrical paths 36A and 36B, and a current (vibration generating current) can be supplied from the current supply section 33 to the ultrasonic transducer 21. In the meantime, the current supply section 33 is composed of, for example, an electric power supply, and a conversion circuit which converts DC current from the electric power supply to a vibration generating current. In addition, the supply controller 35 is, for example, a processor including a CPU (Central Processing Unit) or an ASIC (application specific integrated circuit), and a storage section such as a memory.

Furthermore, a switch 37 is provided within the holding unit 5. One end of a cable-side signal path 41 is connected to the switch 37. The cable-side signal path 41 extends through the inside of the cylindrical case portion 11, the electrical connection ring 45, the transducer case 20, and the inside of the cable 31. In addition, a unit-side signal path 42, which has one end connected to the supply controller 35, is provided in the current control unit 30. By the cable connector 32 of the cable 31 being attached to the current control unit 30, the cable-side signal path 41 is electrically connected to the unit-side signal path 42. Thereby, the switch 37 and supply controller 35 are electrically connected via the cable-side signal path 41 and unit-side signal path 42. At a time of treatment using the ultrasonic vibration by the ultrasonic treatment apparatus 10, an energy operation is input by the pressing of the treatment energy operation button 17, and the switch 37 enters a closed state. Thereby, an operation signal is transmitted from the switch 37 to the supply controller 35 via the cable-side signal path 41 and unit-side signal path 42.

The current control unit 30 is provided with a switching operation section 38 which is electrically connected to the supply controller 35. A switching operation is executed in the switching operation section 38, and, by the switching operation, the switching operation section 38 is changed over between a first switching state and a second switching state. At the time of treatment by the ultrasonic treatment apparatus 10, the switching operation section 38 is changed over to the first switching state. When the switching operation section 38 enters the first switching state, the supply controller 35 controls the current supply section 33 in a treatment mode. In the treatment mode, the supply controller 35 controls the current supply section 33 in such a state that an electric current (AC current) with a fixed amplitude is supplied as a treatment current (vibration generating current) to the ultrasonic transducer 21 only during a period in which the switch 37 is in the closed state (i.e. a period in which a control signal is transmitted from the switch 37).

By the treatment current (current) being supplied to the ultrasonic transducer 21, the ultrasonic vibration (treatment ultrasonic vibration) for use in the treatment occurs in the ultrasonic transducer 21. The ultrasonic vibration occurring in the ultrasonic transducer 21 is transmitted to the ultrasonic probe 7 via the horn member 25. Then, the ultrasonic vibration is transmitted from the proximal direction toward the distal direction in the ultrasonic probe 7, and the treatment section 18 treats a treatment target, such as a biological tissue, by using the transmitted ultrasonic vibration (treatment ultrasonic vibration). By the ultrasonic vibration being transmitted, the ultrasonic probe 7 performs a longitudinal vibration, the vibration direction and transmission direction of which are parallel to the longitudinal axis C. By the jaw 8 being closed relative to the treatment section 18 in the state in which a treated target is positioned between the jaw 8 and treatment section 18, the treated target is grasped between the jaw 8 and treatment section 18. In this state, the treatment section 18 performs the longitudinal vibration by the ultrasonic vibration, and thereby frictional heat occurs between the treated target and the treatment section 18. By the frictional heat, the treated target is coagulated and cut.

As illustrated in FIG. 1, the vibration state inspection system 1 includes an inspection probe 50. In the above-described ultrasonic treatment apparatus 10, from the standpoint of the performance of treatment, it is necessary to properly vibrate the treatment section 18 by the ultrasonic vibration, for example, by vibrating the treatment section 18 with a desired amplitude. Thus, an inspection of the vibration state by the ultrasonic vibration is performed periodically. By the inspection, it becomes possible to detect abnormality (problem) of the handpiece (ultrasonic treatment instrument) 2 including the ultrasonic probe 7, the transducer unit 3 including the ultrasonic transducer 21, and the current control unit 30. The inspection probe 50 is used in order to inspect whether the transducer unit 3 is normally actuated or not, and to inspect whether the current control unit 30 is normally actuated or not. In the inspection of the vibration state, the inspection probe 50, in place of the handpiece 2, is coupled to the transducer unit 3. Specifically, in the inspection of the vibration state by the ultrasonic vibration, the transducer unit 3 is detachably coupled to the proximal direction side of the inspection probe 50.

Figure 4:
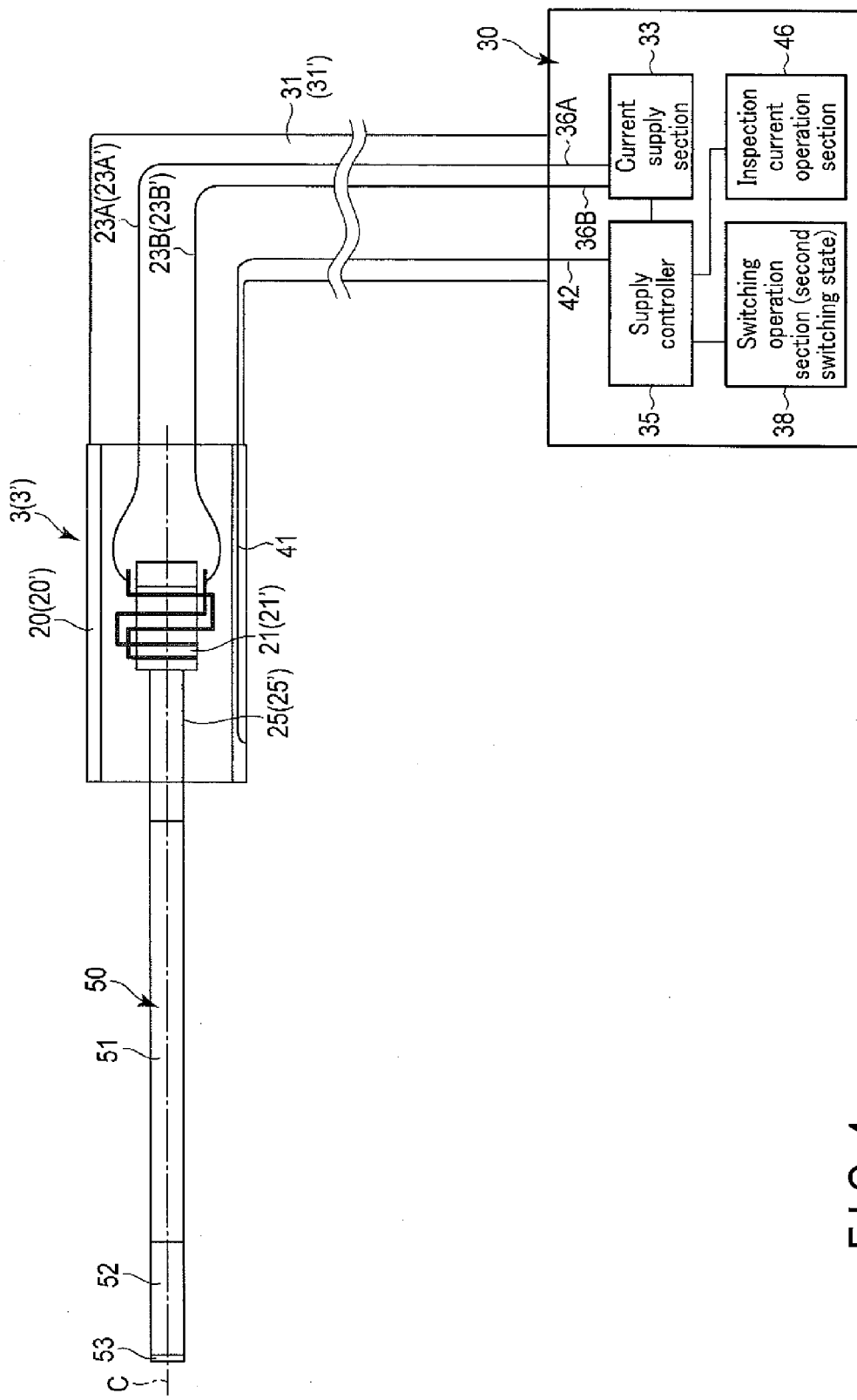
FIG. 4 is a schematic view illustrating an electrical connection state in a state in which an inspection probe according to the first embodiment is coupled to the transducer unit (inspection transducer unit).
Figure 5:
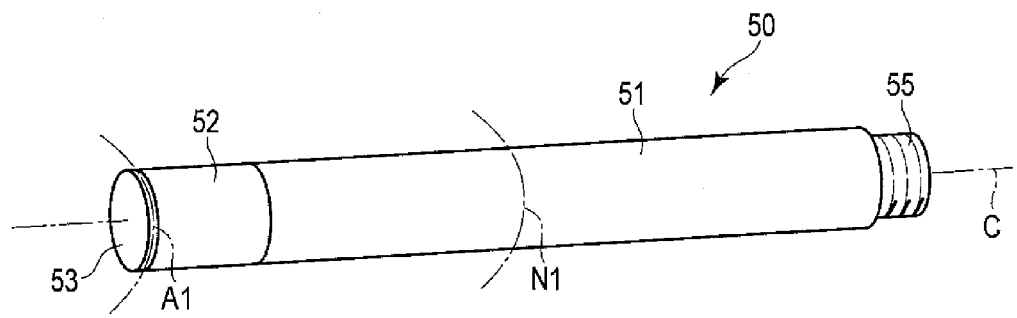
FIG. 5 is a perspective view which schematically illustrates the structure of the inspection probe according to the first embodiment.

FIG. 4 is a view illustrating an electrical connection state in a state in which the inspection probe 50 is coupled to the transducer unit 3. FIG. 5 is a view illustrating the structure of the inspection probe 50. As illustrated in FIG. 2 and FIG. 5, a male screw portion 55 is formed in a proximal portion of the inspection probe 50. In the state in which the transducer unit 3 is coupled to the inspection probe 50, the male screw portion 55 is engaged with the female screw portion 28 of the horn member 25. Thereby, the inspection probe 50 is connected to the distal direction side of the horn member 25.

In addition, as illustrated in FIG. 4, in the inspection of the vibration state, like the case of the time of treatment by the ultrasonic treatment apparatus 10, the cable connector 32 of the cable 31 is attached to the current control unit 30. Thus, the ultrasonic transducer 21, which is the vibration generator, and the current supply section 33 are electrically connected via the electrical wiring lines 23A and 23B and unit-side electrical paths 36A and 36B. However, in the state in which the transducer unit 3 is coupled to the inspection probe 50, the transducer unit 3 is separated from the holding unit 5. Thus, the cable-side signal path 41 is cut off between the electrical connection ring 45 and the transducer case 20. Accordingly, in the state in which the vibrator unit 3 is coupled to the inspection probe 50, the switch 37 and supply controller 35 are not electrically connected.

The current control unit 30 includes an inspection current operation section 46 which is electrically connected to the supply controller 35. In the inspection of the vibration state by the ultrasonic vibration, the switching operation section 38 is changed over to the second switching state. When the switching operation section 38 enters the second switching state, the supply controller 35 controls the current supply section 33 in an inspection mode. In the inspection mode, an inspection current operation is input in the inspection current operation section 46, and thereby an inspection current (vibration generating current) is supplied from the current supply section 33. At this time, the supply controller 35 controls the current supply section 33 in such a state that an electric current (AC current) with a fixed amplitude, which is smaller than the amplitude of the treatment current, is supplied as an inspection current to the ultrasonic transducer 21 only during a predetermined period (e.g. 120 seconds). In the inspection mode in which the switching operation section 38 is in the second switching state, the current supply section 33 is controlled in such a state that the current supply section 33 can output an electric current as an inspection current only when the inspection current operation was input. Accordingly, in the inspection mode, the current supply section 33 is controlled in such a state that the current supply section 33 cannot output a current, such as a treatment current, which is other than the inspection current. By the inspection current (current) being supplied to the ultrasonic transducer 21, the ultrasonic vibration (inspection ultrasonic vibration), which is used for the inspection of the vibration state, occur in the ultrasonic transducer 21. The ultrasonic vibration occurring in the ultrasonic transducer 21 is transmitted to the inspection probe 50 via the horn member 25.

As illustrated in FIG. 5, the inspection probe 50 includes a vibration transmission portion 51 which extends along the longitudinal axis C. In the state in which the inspection probe 50 is connected to the horn member 25, the vibration transmission portion 51 is continuous with the distal direction side of the horn member 25. The vibration transmission portion 51, like the ultrasonic probe 7, is formed of a material with a high vibration transmissibility, such as titanium or duralumin. Thus, in the vibration transmission portion 51, the ultrasonic vibration is transmitted from the horn member 25, and thereby the ultrasonic vibration is transmitted from the proximal direction toward the distal direction.

In addition, the inspection probe 50 includes a vibration damping portion 52 which is continuous with the distal direction side of the vibration transmission portion 51. The vibration damping portion 52 is formed of, for example, a damping alloy, and should preferably have a maximum loss factor of about 0.07 and a damping capacity of 10% or more. An example of the damping alloy, of which the vibration damping portion 52 is formed, is an alloy of iron and aluminum (Al—Fe alloy). When the vibration damping portion 52 is formed of Al—Fe, it is preferable that the Al content is about 6 wt % to 10 wt %, and it is particularly preferable that the Al content is about 8 wt %. In addition, the damping alloy, of which the vibration damping portion 52 is formed, has high rigidity.

The vibration damping portion 52 is formed of the damping alloy. Thus, with the transmission of the ultrasonic vibration from the vibration transmission portion 51, the vibration damping portion 52 vibrates in a manner to follow the vibration transmission portion 51. At this time, the ultrasonic vibration (inspection ultrasonic vibration) is absorbed by the vibration damping portion 52 that is formed of the damping alloy, and the vibration energy of the ultrasonic vibration is lost. By the loss of the vibration energy, the ultrasonic vibration is damped in the vibration damping portion 52. The causes of the loss of vibration energy in the vibration damping portion 52 vary depending on the kind of damping alloy. The following causes may be mentioned. In a certain kind of damping alloy, the vibration energy is lost by damping due to, e.g. a viscous flow at an interface between a matrix phase and a precipitated phase (complex type). In another kind of damping alloy, a static hysteresis phenomenon is caused to occur by a glide dislocation in a crystal, and the vibration energy is lost by the static hysteresis phenomenon (dislocation type). In still another kind of damping alloy, an internal friction occurs due to an irreversible movement of a magnetic domain wall, and the vibration energy is lost by the internal friction (ferromagnetic type). In still another kind of damping alloy, the vibration energy is lost by the occurrence of twin deformation (twin type). In still another kind of damping alloy, the above-described causes are combined, and the vibration energy is lost.

In the meantime, it is preferable that the damping alloy, of which the vibration damping portion 52 is formed, has a strength which is substantially equal to or higher than the strength of iron, and has a specific gravity which is less than the specific gravity of iron by about 10%. It is also preferable that the damping alloy can easily be subjected to forging, press-forming, cutting work, etc. Furthermore, it is preferable that the damping alloy has a stable oxidation-resistance function by an oxide film in environments of both low temperatures and high temperatures, and is robust to a brittle fracture in a normal-temperature environment. In addition, although the damping alloy is an electrically conductive metal, it is preferable that the electrical resistance value is about several times (e.g. four times) higher than that of iron. From the above-described conditions, as the damping alloy of which the vibration damping portion 52 is formed, it uses one made of, in addition to the Al—Fe alloy of the complex type, for instance, a complex-type Al—Zn alloy, twin-type Ni—Ti alloy, Cu—Al—Ni alloy, Mn—Cu alloy, Mn—Cu—Ni—Fe alloy, etc.

In the vibration damping portion 52, the lost vibration energy is converted to heat energy. Thus, by the ultrasonic vibration (inspection ultrasonic vibration) being transmitted to the vibration damping portion 52, heat occurs in the vibration damping portion 52. In addition, the inspection probe 50 includes a heat radiation portion 53 to which the heat produced in the vibration damping portion 52 is transferred, and which radiates the transferred heat to the air. The heat radiation portion is, for example, a blackbody coating material which is coated on a distal surface of the vibration damping portion 52. The temperature of the heat radiation portion 53 varies in accordance with a conversion amount from vibration energy to heat energy in the vibration damping portion 52. In addition, the heat radiation amount from the heat radiation portion 53 varies in accordance with a variation in temperature of the heat radiation portion 53. Accordingly the heat radiation amount from the heat radiation portion 53 varies in accordance with the conversion amount to heat energy in the vibration damping portion 52. Specifically, the heat radiation portion 53 is an index section serving as an index indicating the conversion amount to heat energy in the vibration damping portion 52.

Here, when the inspection probe 50 is vibrated in a predetermined vibration state by the ultrasonic vibration (for example, when the inspection probe 50 is vibrated only for a predetermined time in a state in which the vibration transmission portion 51 has a fixed amplitude), the conversion amount from the vibration energy to heat energy in the vibration damping portion 52 is kept within a predetermined range. Since the conversion amount to heat energy in the vibration damping portion 52 falls within the predetermined range, when the inspection probe 50 is vibrated in the predetermined vibration state, the temperature of the heat radiation portion 53 also falls within a predetermined range, and the heat radiation amount from the heat radiation portion 53 is also kept within a predetermined range. Therefore, when the heat radiation amount from the heat radiation portion 53 falls out of the predetermined range, it is confirmed that the inspection probe 50 does not vibrate in the predetermined vibration state.

In addition, in the state in which the inspection probe 50 vibrates by the ultrasonic vibration (in a predetermined frequency range), an antinode position, which is located most distally among antinode positions of the ultrasonic vibration, is set as a foremost distal antinode position A1, and a node position, which is located most distally among node positions of the ultrasonic vibration, is set as a foremost distal node position N1. In the present embodiment, the foremost distal-end antinode position A1 is located near the heat radiation section 53 (near the distal end of the inspection probe 50). The foremost distal node position N1 is located on the vibration transmission portion 51. Accordingly, a boundary position between the vibration transmission portion 51 and the vibration damping portion 52 is located on the proximal direction side with respect to the foremost distal antinode position A1, and is located on the distal direction side with respect to the foremost distal node position N1. Thus, the boundary position between the vibration transmission portion 51 and vibration damping portion 52 is located at a position different from the antinode positions of the ultrasonic vibration including the foremost distal antinode position A1. Since the boundary position between the vibration transmission portion 51 and the vibration damping portion 52 is located at a position different from the antinode positions where a stress due to the ultrasonic vibration becomes zero, a stress due to the ultrasonic vibration occurs at the boundary position between the vibration transmission portion 51 and the vibration damping portion 52. Since the stress occurs at the boundary position between the vibration transmission portion 51 and the vibration damping portion 52, the vibration energy is properly lost in the vibration damping portion 52, and the lost vibration energy is properly converted to heat energy.

Furthermore, since the boundary position between the vibration transmission portion 51 and the vibration damping portion 52 is located between the foremost distal antinode position A1 and foremost distal node position N1 in the axis-parallel direction that is parallel to the longitudinal axis C, the dimension of the vibration damping portion 52 in the axis-parallel direction is less than a ¼ wavelength of the ultrasonic vibration, and does not become excessively large. Since the dimension of the vibration damping section 52 in the axis-parallel direction does not become excessively large, the vibration energy is not excessively lost in the vibration damping portion 52. Thus, with the transmission of the ultrasonic vibration, the vibration damping portion 52 properly vibrates in a manner to follow the vibration transmission portion 51. Additionally, since the dimension of the vibration damping portion 52 in the axis-parallel direction does not become excessively large, the heat produced in the vibration damping portion 52 is properly transferred to the heat radiation portion 53. Besides, the dimension of the vibration damping portion 52 in the axis-parallel direction does not become excessively small. Thus, vibration energy is converted to heat energy in the vibration damping portion 52 by a conversion amount or more, which is necessary for securing the precision of the inspection. Thereby, a proper inspection is performed by measuring the heat radiation amount from the heat radiation portion 53.

Figure 6:
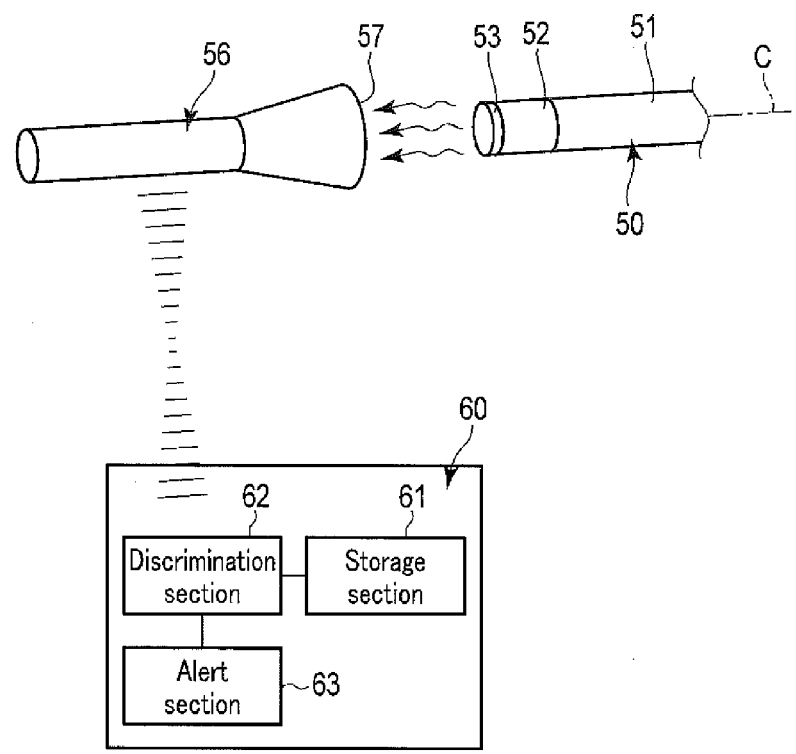
FIG. 6 is a schematic view illustrating a state in which a heat radiation amount from a heat radiation section according to the first embodiment is measured.

As illustrated in FIG. 1, the vibration state inspection system 1 includes an infrared camera 56 which is a measuring unit, and a discrimination processing unit 60 which is a processing device. FIG. 6 is a view illustrating a state in which the heat radiation amount from the heat radiation portion 53 is measured. As illustrated in FIG. 6, the infrared camera 56 includes a heat measuring section 57 which measures the heat radiation amount from the heat radiation portion 53 as a physical amount. In the measurement of the heat radiation amount, the measuring is performed in the state in which the heat measuring section 57 of the infrared camera 56 is opposed to the heat radiation portion 53 of the inspection probe 50. Specifically, a variation of the heat radiation portion 53, which is the index section, is detected by the infrared camera 56 that is the measuring unit, and the heat radiation amount, which is the physical amount varying based on the conversion amount to heat energy in the vibration damping portion 52, is measured.

The discrimination processing unit 60 can communicate with the infrared camera 56 by wireless communication or via a communication line. In addition, the discrimination processing unit 60 can communicate with the current control unit 30 by wireless communication or via a communication line. The discrimination processing unit 60 includes a storage section 61, such as a memory, which stores information, etc. Here, a state, in which both the transducer unit 3 and the current control unit 30 are normally actuated, is defined as a normal state. The storage section 61 stores a relationship in the normal state between the inspection current, which is supplied from the current supply section 33, and the heat radiation amount which is the measured physical amount. In the normal state, a current (AC current) of a fixed amplitude is supplied as an inspection current to the ultrasonic transducer 21 from the current supply section 33 only for a predetermined time (e.g. 120 seconds). Thereby, the inspection probe 50 vibrates in a predetermined vibration state. Thus, as described above, the temperature of the heat radiation portion 53 also fails within the predetermined range, and the heat radiation amount from the heat radiation portion 53 is also kept within the predetermined range. Such a relationship between the inspection current and heat radiation amount is stored in the storage section 61.

The discrimination processing unit 60 includes a discrimination section 62 which is electrically connected to the storage section 61. The discrimination section 62 is, for example, a processor including a CPU or an ASIC. The discrimination section 62 discriminates whether the transducer unit 3 including the ultrasonic transducer 21, and the current control unit 30 are normally actuated or not. A measurement result of the heat radiation amount from the heat radiation portion 53, which was measured by the infrared camera 56, is transmitted to the discrimination section 62 from the infrared camera 56 by communication. In addition, information relating to the inspection current, which is supplied from the current supply section 33, is transmitted to the discrimination section 62 from the current control unit 30 by communication. The discrimination section 62 makes' a discrimination, based on the measurement result of the heat radiation amount, the information relating to the inspection current, and the relationship in the normal state between the inspection current and the heat radiation amount, which is stored in the storage section 61. For example, it is assumed that the information indicating that a current (AC current) of a fixed amplitude was supplied as the inspection current to the ultrasonic transducer 21 from the current supply section 33 only for a predetermined time (e.g. 120 seconds) was transmitted to the discrimination section 62. At this time, if the measured heat radiation amount falls within the predetermined range, it is determined that the transducer unit 3 and current control unit 30 are in the normal state in which they are normally operated. On the other hand, if the measured heat radiation amount falls out of the predetermined range, it is determined that abnormality (problem) occurs in the transducer unit 3 or the current control unit 30, and that the transducer unit 3 or current control unit 30 is not in the normal state.

Furthermore, the discrimination processing unit 60 includes an alert section 63 which is electrically connected to the discrimination section 62. The alert section 63 is a lamp, a buzzer, or the like. If the discrimination section 62 determined that abnormality (problem) occurs in the transducer unit 3 or current control unit 30, the alert section 63 displays an alert.

As illustrated in FIG. 1, the vibration state inspection system 1 includes an inspection transducer unit 3'. The inspection transducer unit 3' is detachably coupled to the proximal direction side of the inspection probe 50. In addition, the inspection transducer unit 3' is detachably connected to the current control unit 30 via an inspection cable 31'. The inspection transducer unit 3' is used only for an inspection of the vibration state by the ultrasonic vibration, and is not used for treatment by the ultrasonic vibration. Hence, the handpiece 2 is not coupled to the inspection transducer unit 3'. The inspection transducer unit 3' has the same structure as the transducer unit 3. Thus, referring to FIG. 2 and FIG. 4, the inspection transducer unit 3' is described. Incidentally, in FIG. 2 and FIG. 4, the parts relating to the inspection transducer unit 3' are denoted by reference numerals in parentheses.

The inspection transducer unit 3' includes an inspection transducer case 20' which has the same structure as the transducer case 20, and an inspection ultrasonic transducer 21' which is an inspection vibration generator with the same structure as the ultrasonic transducer 21. The inspection ultrasonic transducer 21' includes piezoelectric elements 22A' to 22D'. The inspection ultrasonic transducer 21' is supplied with an inspection current, thereby generating an ultrasonic vibration (inspection ultrasonic vibration). In addition, the inspection transducer unit 3' includes an inspection horn member 25' which has the same structure as the horn member 25. The inspection horn member 25' includes a transducer attachment portion 26', a cross-sectional area varying portion 27', and a female screw portion 28'. Furthermore, one end of each of electric wiring lines 23A', 23B' is connected to the inspection ultrasonic transducer 21'. A cable connector 32'. of the inspection cable 31' is attached to the current control unit 30, and thereby the electrical wiring line 23A' is electrically connected to the unit-side electrical path 36A, and the unit-side electrical path 36B is electrically connected to the electrical wiring line 23B'. Thereby, the current supply section 33 and inspection ultrasonic transducer 21' are electrically connected, and the current can be supplied from the current supply section 33 to the inspection ultrasonic transducer 21'.

The inspection transducer unit 3' is actuated in the same state as the transducer unit 3 that is normally actuated. Specifically, in the state in which an inspection current is supplied from the current control unit 30 that is normally actuated, the inspection transducer unit 3' is normally actuated. Accordingly, by the inspection current being supplied from the current control unit 30 that is normally actuated, the ultrasonic vibration (inspection ultrasonic vibration) occurs in the inspection ultrasonic transducer 21', and the inspection probe 50 vibrates in a predetermined vibration state (for example, the inspection probe 50 vibrates only for a predetermined time in a state in which the vibration transmission portion 51 has a fixed amplitude). By the inspection probe 50 vibrating in the predetermined vibration state, the temperature of the heat radiation portion 53 also falls within a predetermined range, and the heat radiation amount from the heat radiation portion 53 is also kept within a predetermined range, as described above. On the other hand, when abnormality (problem) occurs in the current control unit 30, the inspection current is not properly supplied from the current supply section 33 to the inspection ultrasonic transducer 21'. Consequently, the inspection probe 50 does not vibrate in the predetermined vibration state, and the heat radiation amount from the heat radiation portion 53 falls out of the predetermined range.

Next, the functions and advantageous effects of the ultrasonic treatment apparatus 10 and vibration state inspection system 1 are described. At a time of treating a treated target, such as a living body tissue, by using an ultrasonic vibration (treatment ultrasonic vibration) the handpiece 2 is coupled to the transducer unit 3, and the transducer unit 3 is connected to the current control unit 30 via the cable 31. Thereby, the ultrasonic treatment apparatus 10 is constituted. At this time, the switching operation section 38 enters the first switching state, and the supply controller 35 controls the current supply section 33 in the treatment mode. In addition, the sheath 6, the ultrasonic probe 7 and the jaw 8 are inserted in a body cavity, and a treated target is positioned between the jaw 8 and treatment section 18. In this state, the movable handle 13 is closed relative to the stationary handle 12. Thereby, the jaw 8 is closed relative to the treatment section 18, and the treated target is grasped between the jaw 8 and treatment section 18. In the state in which the treated target is grasped, an energy operation is input by the treatment energy operation button 17, and the switch 37 is set in the closed state. Thereby, an operation signal is transmitted to the supply controller 35, and the supply controller 35 controls the current supply section 33 in the treatment mode. At this time, the supply controller 35 controls the current supply section 33 in such a state that an electric current (AC current) with a fixed amplitude is supplied as a treatment current to the ultrasonic transducer 21 only during a period in which the switch 37 is in the closed state (i.e. a period in which a control signal is transmitted from the switch 37).

By the treatment current (current) being supplied to the ultrasonic transducer 21, the ultrasonic vibration (treatment ultrasonic vibration) for use in the treatment occurs in the ultrasonic transducer 21. The ultrasonic vibration occurring in the ultrasonic transducer 21 is transmitted to the ultrasonic probe 7 via the horn member 25. Then, the ultrasonic vibration is transmitted from the proximal direction toward the distal direction in the ultrasonic probe 7, and the treatment section 18 treats the treated target, such as a living body tissue, by using the transmitted ultrasonic vibration (treatment ultrasonic vibration). At this time, the ultrasonic probe 7 performs longitudinal vibration with a fixed amplitude only during a period in which the switch 37 is in the closed state (i.e. a period in which a control signal is transmitted from the switch 37). In the state in which the treated target is positioned between the jaw 8 and treatment section 18, the treatment section 18 performs longitudinal vibration, and thereby the treated target is coagulated and cut by frictional heat occurring between the treated target and the treatment section 18.

Figure 7:
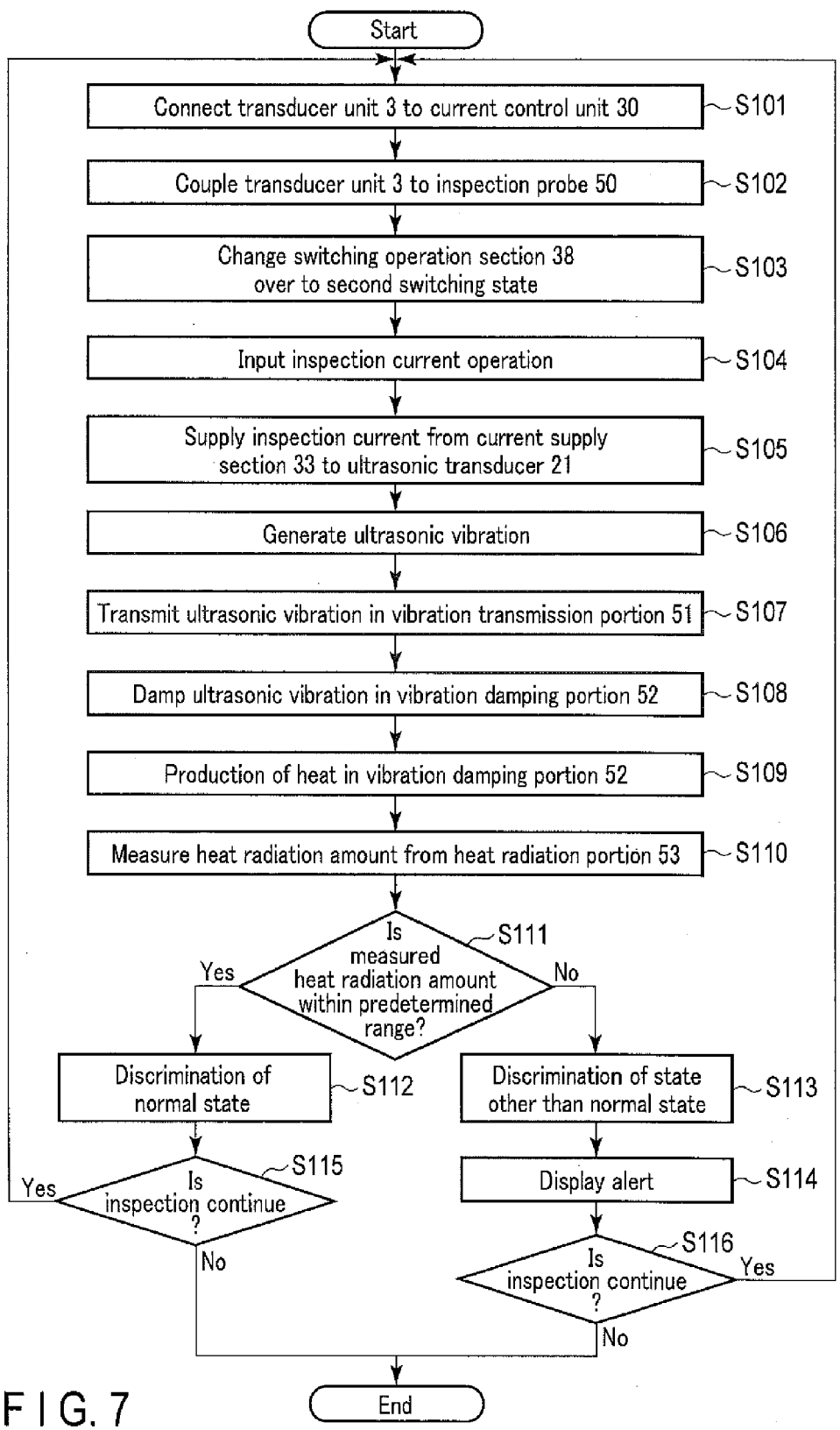
FIG. 7 is a flowchart illustrating a method of inspecting whether the transducer unit and a current control unit according to the first embodiment are in a normal state in which they are normally actuated.

At a time of inspecting the vibration state by the ultrasonic vibration, it is first inspected whether the transducer unit 3 and current control unit 30 are in the normal state in which they are normally actuated. FIG. 7 is a view illustrating a method of inspecting whether the transducer unit 3 and current control unit 30 are in the normal state in which they are normally actuated. As illustrated in FIG. 7, in the inspection as to the normal state or otherwise, the transducer unit 3 is first connected to the current control unit 30 via the cable 31 (step S101). Then, the transducer unit 3 is coupled to the proximal direction side of the inspection probe 50 (step S102). In addition, in the current control unit 30, the switching operation section 38 is changed over to the second switching state (step S103). Thereby, the supply controller 35 controls the current supply section 33 in the inspection mode. In the meantime, such a configuration is adopted that the switching operation of the switching operation section 38 between the first switching state and second switching state cannot easily be executed by a surgeon or the like, who treats the treated target, but can be executed by only an inspector who inspects the vibration state. Thereby, at the time of treatment using the ultrasonic vibration, it is possible to effectively prevent the supply controller 35 from being switched from the treatment mode to the inspection mode.

Then, in the inspection mode, an inspection current operation is input in the inspection current operation section 46 (step S104). Thereby, an inspection current is supplied from the current supply section 33 to the ultrasonic transducer 21 that is the vibration generator (step S105). At this time, the supply controller 35 controls the current supply section 33 in such a state that an electric current (AC current) with a fixed amplitude, which is lower than the amplitude of the treatment current, is supplied as an inspection current (vibration generating current) to the ultrasonic transducer 21 only for a predetermined time (e.g. 120 seconds). In addition, in the inspection mode in which the switching operation section 38 enters the second switching mode, the current supply section 33 is controlled in such a state that the current supply section 33 cannot output a current, such as a treatment current, which is other than the inspection current. By the inspection current (current) being supplied to the ultrasonic transducer 21, the ultrasonic vibration (inspection ultrasonic vibration), which is used for the inspection of the vibration state, occurs in the ultrasonic transducer 21 (step S106). The ultrasonic vibration occurring in the ultrasonic transducer 21 is transmitted to the inspection probe 50 via the horn member 25. The amplitude of the ultrasonic vibration is increased by the cross-sectional area varying portion 27 of the horn member 25.

Then, in the vibration transmission portion 51 of the inspection probe 50, the ultrasonic vibration is transmitted from the proximal direction toward the distal direction (step S107). Thereby, the ultrasonic vibration is transmitted to the vibration damping portion 52, and the vibration damping portion 52 vibrates in a manner to follow the vibration transmission portion 51. With the vibration damping portion 52 vibrating, the vibration damping portion 52 causes the vibration energy of the ultrasonic vibration to be lost, and damps the ultrasonic vibration (step S108). Further, by the vibration damping portion 52, the lost vibration energy is converted to heat energy, and heat occurs (step S109). The heat produced in the vibration damping portion 52 is transferred to the heat radiation portion 53 that is the index section.

When the inspection probe 50 vibrates in a predetermined frequency range (vibration state), the boundary position between the vibration transmission portion 51 and the vibration damping portion 52 is located at a position different from the antinode positions. Thus, a stress due to ultrasonic vibration occurs at the boundary position between the vibration transmission portion 51 and the vibration damping portion 52. Since the stress occurs at the boundary position between the vibration transmission portion 51 and the vibration damping portion 52, the vibration energy is properly lost in the vibration damping portion 52, and the lost vibration energy is properly converted to heat energy. In addition, since the dimension of the vibration damping portion 52 in the axis-parallel direction, which is parallel to the longitudinal axis C, does not become excessively large, the vibration energy is not excessively lost in the vibration damping portion 52. Thus, with the transmission of the ultrasonic vibration, the vibration damping portion 52 properly vibrates in a manner to follow the vibration transmission portion 51. Additionally, since the dimension of the vibration damping portion 52 in the axis-parallel direction does not become excessively large, the heat produced in the vibration damping portion 52 is properly transferred to the heat radiation portion 53. Besides, the dimension of the vibration damping portion 52 in the axis-parallel direction does not become excessively small. Thus, vibration energy is converted to heat energy in the vibration damping portion 52 in the normal state by a conversion amount or more, which is necessary for securing the precision of the inspection. Thereby, a proper inspection is performed by measuring the heat radiation amount from the heat radiation portion 53. Moreover, the amplitude of the ultrasonic vibration is increased by the cross-sectional area varying portion 27 of the horn member 25. With the increase of the amplitude of the ultrasonic vibration, the conversion amount to heat energy in the vibration damping portion 52 increases. Thereby, the precision of the inspection is further enhanced.

Here, in the normal state in which the transducer unit 3 and current control unit 30 are normally actuated, the ultrasonic vibration is transmitted to the inspection probe 50, and thereby the inspection probe 50 vibrates in a predetermined vibration state (for example, the inspection probe 50 vibrates only for a predetermined time in a state in which the vibration transmission portion 51 has a fixed amplitude). When the inspection probe 50 vibrates in the predetermined vibration state, the conversion amount from the vibration energy to heat energy in the vibration damping portion 52 is kept within a predetermined range. Since the conversion amount to heat energy in the vibration damping portion 52 falls within the predetermined range, when the inspection probe 50 is vibrated in the predetermined vibration state, the temperature of the heat radiation portion 53 also falls within a predetermined range, and the heat radiation amount from the heat radiation portion 53 is also kept within a predetermined range. On the other hand, when abnormality (problem) occurs in the transducer unit 3 or current control unit 30 (when not in the normal state), even if the ultrasonic vibration is transmitted to the inspection probe 50, the inspection probe 50 vibrates in a vibration state which is different from the predetermined vibration state. Specifically, due to the occurrence of abnormality (problem) in the transducer unit 3 or the current control unit 30, the inspection probe 50 fails to vibrate in the predetermined vibration state. Consequently, the conversion amount to heat energy in the vibration damping portion 52 falls out of the predetermined range. Hence, the temperature of the heat radiation portion 53 falls out of the predetermined range, and the heat radiation amount from the heat radiation portion 53 also falls out of the predetermined range.

In the determination of the normal state or otherwise, the heat radiation amount from the heat radiation portion 53 is measured by the infrared camera 56 that is the measuring unit (step S110). Thereby, a variation of the heat radiation portion 53 that is the index section is detected. Then, based on the measured heat radiation amount, the discrimination section 62 discriminates whether the transducer unit 3 and current control unit 30 are in the normal state in which they are normally actuated. Specifically, based on the detection result of the variation of the heat radiation portion 53 that is the index section, a discrimination of the normal state or otherwise is made. At this time, the discrimination section 62 determines whether the measured heat radiation amount is within the predetermined range or not (step S111). The determination in step S111 is made based on the relationship in the normal state between the inspection current and the heat radiation amount, which is stored in the storage section 61. If the measured heat radiation amount is within the predetermined range (step S111—Yes), it is discriminated that the transducer unit 3 and current control unit 30 are in the normal state in which they are normally operated (step S112). On the other hand, if the measured heat radiation amount is out of the predetermined range (step S111—No), it is discriminated that abnormality (problem) occurs in the transducer unit 3 or current control unit 30, and the transducer unit 3 or current control unit 30 is not in the normal state (step S113). If a state other than the normal state is discriminated, an alert is displayed by the alert section 63 (step S114). Then, if the inspection is not continued (step S115—No and step S116—No), the inspection is finished.

As described above, in the present embodiment, by using the inspection probe 50, the discrimination as to whether the transducer unit 3 and current control unit 30 are normally actuated or not can properly be made. In addition, in the present embodiment, the discrimination of the normal state or otherwise is made by detecting the variation of the heat radiation portion 53 serving as an index indicating the conversion amount from vibration energy to heat energy in the vibration damping portion 52. Specifically, in the discrimination as to the normal state or otherwise, the vibration state of the inspection probe 50 is not directly measured. Thus, a laser, a microscope or the like is not used in the discrimination of the normal state or otherwise. Therefore, it is possible to easily discriminate whether the transducer unit 3 and current control unit 30 are normally actuated or not.

Figure 8:
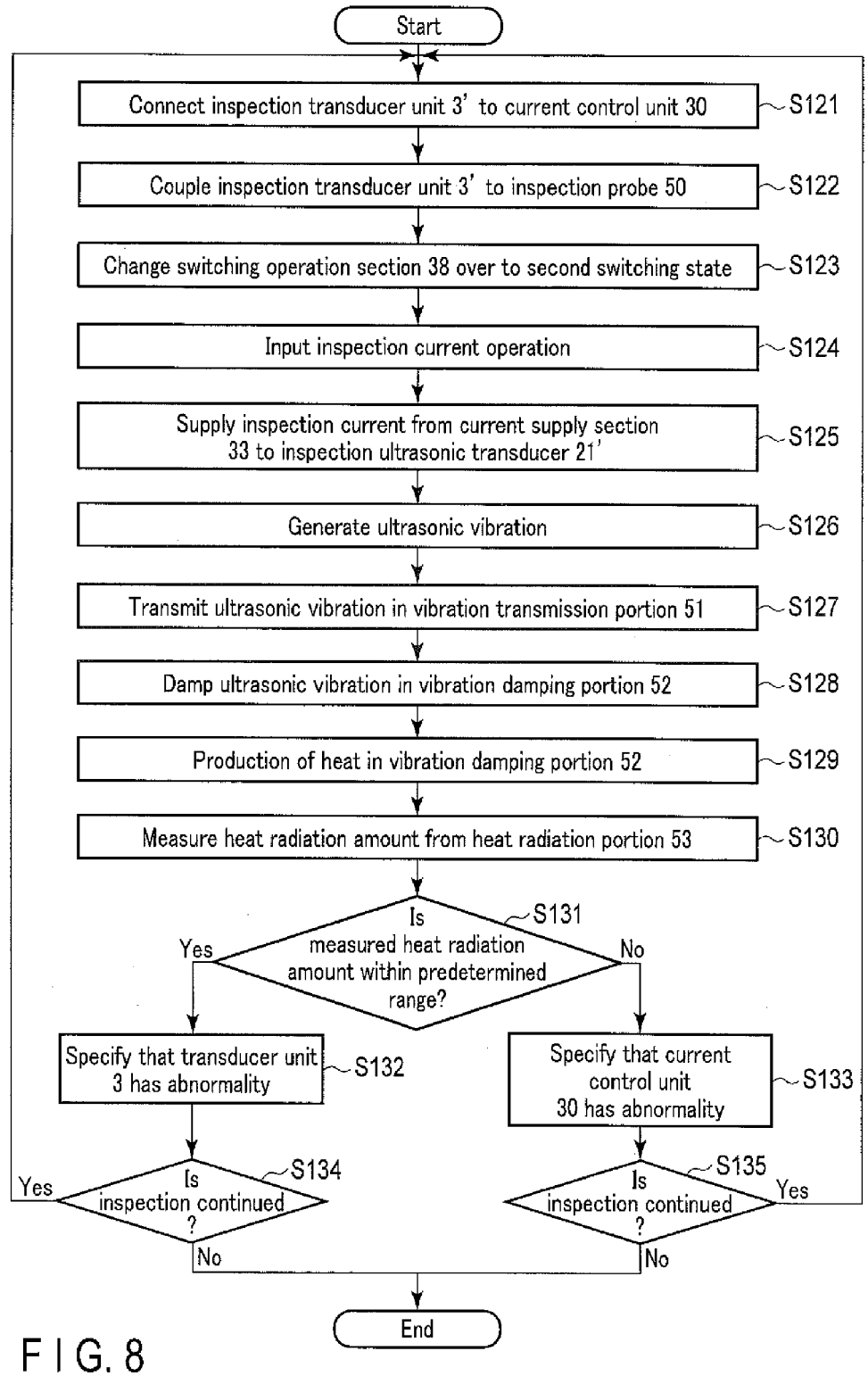
FIG. 8 is a flowchart illustrating a method of specifying whether abnormality (problem) occurs in either the transducer unit or the current control unit according to the first embodiment.

FIG. 8 is a view illustrating a method of specifying whether abnormality (problem) occurs in the transducer unit 3 or the current control unit 30, when it was discriminated that the transducer unit 3 or current control unit 30 is not in the normal state. When not in the normal state, it is important to specify, in the inspection of the vibrating state by the ultrasonic vibration, whether abnormality occurs in the transducer unit 3 or not, and whether abnormality occurs in the current control unit 30 or not. For example, if the current control unit 30 is normally actuated and abnormality occurs only in the transducer unit 3, it should suffice if only the transducer unit 3 is replaced for use in the treatment, etc. after the inspection, and there is no need to replace the current control unit 30.

As illustrated in FIG. 8, in specifying a unit (part) in which abnormality occurs, the inspection transducer unit 3' is first connected to the current control unit 30 via the inspection cable 31' (step S121). Then, the inspection transducer unit 3' is coupled to the proximal direction side of the inspection probe 50 (step S122). In addition, in the current control unit 30, the switching operation section 38 is changed over to the second switching state (step S123). Thereby, the supply controller 35 controls the current supply section 33 in the inspection mode. In the meantime, the transducer unit 3 is not used in specifying the unit in which abnormality occurs.

Then, in the inspection mode, an inspection current operation is input in the inspection current operation section 46 (step S124). Thereby, an inspection current is supplied from the current supply section 33 to the inspection ultrasonic transducer 21' that is the inspection vibration generator (step S125). At this time, in the same state as the inspection of the normal state or otherwise, the inspection current is supplied from the current supply section 33 to the inspection ultrasonic transducer 21'. By the inspection current (current) being supplied to the inspection ultrasonic transducer 21', the ultrasonic vibration (inspection ultrasonic vibration), which is used for the inspection of the vibration state, occurs in the inspection ultrasonic transducer 21' (step S126). The ultrasonic vibration occurring in the inspection ultrasonic transducer 21' is transmitted to the inspection probe 50 via the inspection horn member 25'. Then, in the vibration transmission portion 51 of the inspection probe 50, the ultrasonic vibration is transmitted from the proximal direction toward the distal direction (step S127). With the vibration damping portion 52 vibrating, the vibration damping portion 52 causes the vibration energy of the ultrasonic vibration to be lost, and damps the ultrasonic vibration (step S128). Further, by the vibration damping portion 52, the lost vibration energy is converted to heat energy, and heat occurs (step S129). The heat produced in the vibration damping portion 52 is transferred to the heat radiation portion 53 that is the index section.

The inspection transducer unit 3' is actuated in the same state as the transducer unit 3 that is normally actuated. Accordingly, when there is no abnormality in the current control unit 30 and the current control unit 30 is normally actuated, the inspection current is supplied to the inspection ultrasonic transducer 21', and thereby the inspection probe 50 vibrates in the predetermined vibration state (for example, the inspection probe 50 vibrates only for a predetermined time in a state in which the vibration transmission portion 51 has a fixed amplitude). As described above, with the inspection probe 50 vibrating in the predetermined vibration state, the temperature of the heat radiation portion 53 also falls within the predetermined range, and the heat radiation amount from the heat radiation portion 53 is also kept within the predetermined range. In this case, while the heat radiation amount falls out of the predetermined range in the inspection using the transducer unit 3, the heat radiation amount falls within the predetermined range in the inspection using the inspection transducer unit 3'. Accordingly, it turns out that abnormality (problem) occurs in the transducer unit 3. On the other hand, when abnormality (problem)

occurs in the current control unit 30, the inspection current is not properly supplied from the current supply section 33 to the inspection ultrasonic transducer 21'. Thus, the inspection probe 50 fails to vibrate in the predetermined vibration state, and the heat radiation amount from the heat radiation portion 53 falls out of the predetermined range.

In the specifying of the unit in which abnormality occurs, the heat radiation amount from the heat radiation portion 53 is measured by the infrared camera 56 that is the measuring unit (step S130). Thereby, a variation of the heat radiation portion 53 that is the index section is detected. Then, based on the measured heat radiation amount, the discrimination section 62 specifies whether abnormality occurs in the transducer unit 3 or abnormality occurs in the current control unit 30. Specifically, based on the detection result of the variation of the heat radiation portion 53 that is the index section, the unit (transducer unit 3 or current control unit 30) in which abnormality occurs is specified. At this time, the discrimination section 62 determines whether the measured heat radiation amount is within the predetermined range or not (step S131). The determination in step S111 is made based on the relationship in the normal state between the inspection current and heat radiation amount, which is stored in the storage section 61. If the measured heat radiation amount is within the predetermined range (step S131—Yes), it is specified that abnormality occurs in the transducer unit 3 (step S132). On the other hand, if the measured heat radiation amount is out of the predetermined range (step S131—No), it is specified that abnormality occurs in the current control unit 30 (step S133). Then, if the inspection is not continued (step S134—No and step S135—No), the inspection is finished.

As described above, in the present embodiment, by using the inspection probe 50 and inspection transducer unit 3', the unit (transducer unit 3 or current control unit 30) in which abnormality occurs can properly be specified. In addition, in the present embodiment, the unit in which abnormality occurs is specified by detecting the variation of the heat radiation portion 53 serving as an index indicating the conversion amount from vibration energy to heat energy in the vibration damping portion 52. Therefore, a laser, a microscope or the like is not used in specifying the unit in which abnormality occurs, and the unit in which abnormality occurs can easily be specified.

Second Embodiment

Next, a second embodiment of the present invention is described with reference to FIG. 9 and FIG. 10. In the second embodiment, the structure of the first embodiment is modified as described below. Incidentally, the same parts as in the first embodiment are denoted by like reference numerals, and a description thereof is omitted.

Figure 9:
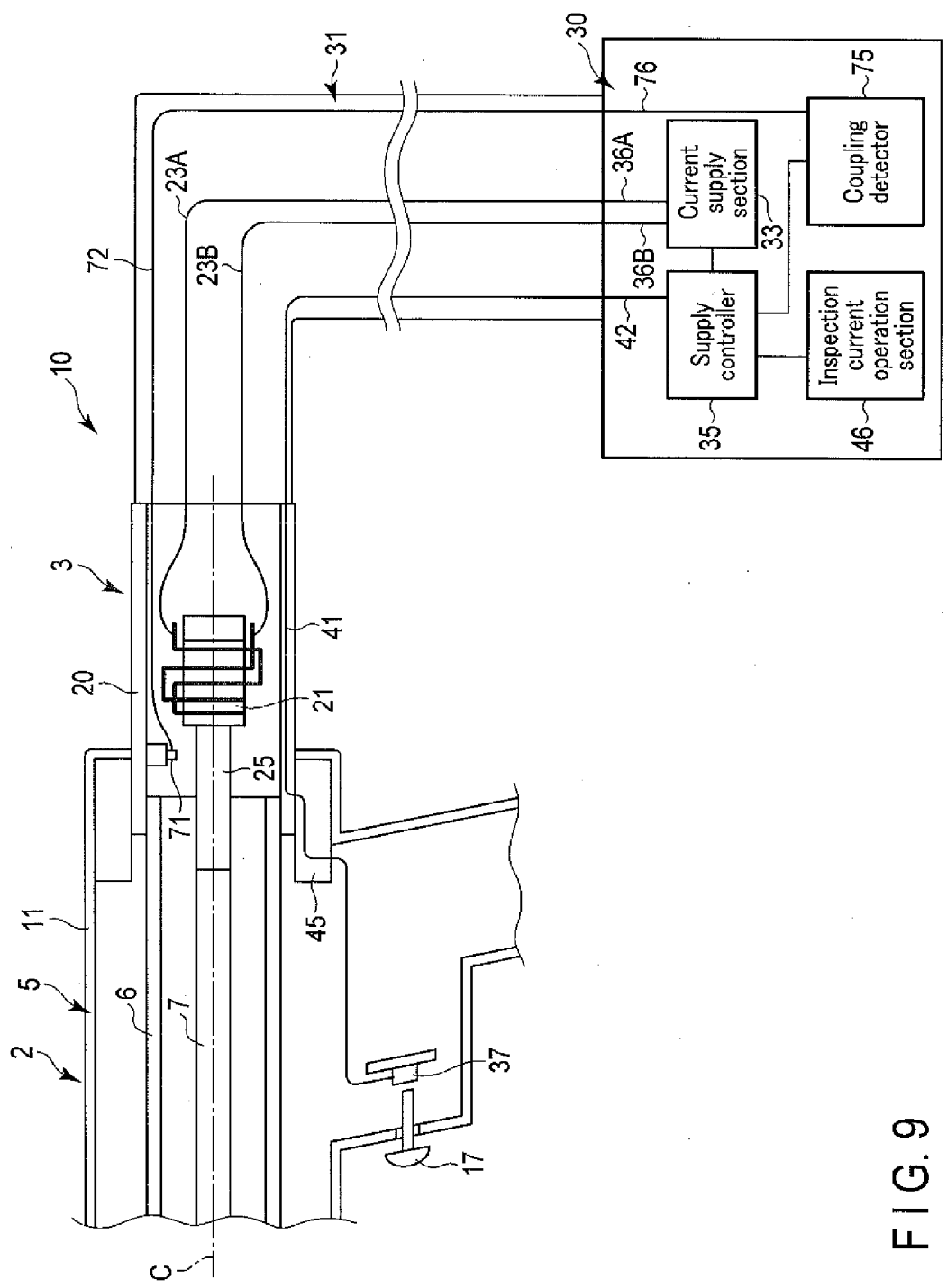
FIG. 9 is a schematic view illustrating an electrical connection state of an ultrasonic treatment apparatus according to a second embodiment.

FIG. 9 is a view illustrating an electrical connection state of an ultrasonic treatment apparatus 10 of the present embodiment. As illustrated in FIG. 9, in the present embodiment, like the first embodiment, at the time of treatment using an ultrasonic vibration, the transducer unit 3 is coupled to the handpiece 2, and the transducer unit 3 is connected to the current control unit 30 via the cable 31. Thereby, the ultrasonic treatment apparatus 10 is constituted. In this embodiment, the transducer unit 3 is provided with a detection switch 71. The detection switch 71 is attached to the transducer case 20. One end of a cable-side signal line 72 is connected to the detection switch 71. The cable-side signal line 72 extends through the inside of the transducer case 20 and the inside of the cable 31. In the detection switch 71, an urging force acts for setting the detection switch 71 in the open state. At a treatment time when the handpiece 2 is coupled to the transducer unit 3 (in the ultrasonic treatment apparatus 10), no acting force or the like acts on the detection switch 71 from the handpiece 2, and the detection switch 71 is set in the open state by the urging force.

In the present embodiment, the switching operation section 38 is not provided in the current control unit 30. Instead, a coupling detector 75, which is electrically connected to the supply controller 35, is provided in the current control unit 30. The coupling detector 75 is formed of, for example, a detection circuit. In addition, in the current control unit 30, there is provided a unit-side signal transmitting portion 76 which has one end connected to the coupling detector 75. The cable connector 32 of the cable 31 is attached to the current control unit 30, and thereby the cable-side signal line 72 is electrically connected to the unit-side signal transmitting portion 76. Thereby, the detection switch 71 and coupling detector 75 are electrically connected via the cable-side signal line 72 and unit-side signal transmitting portion 76.

Figure 10:
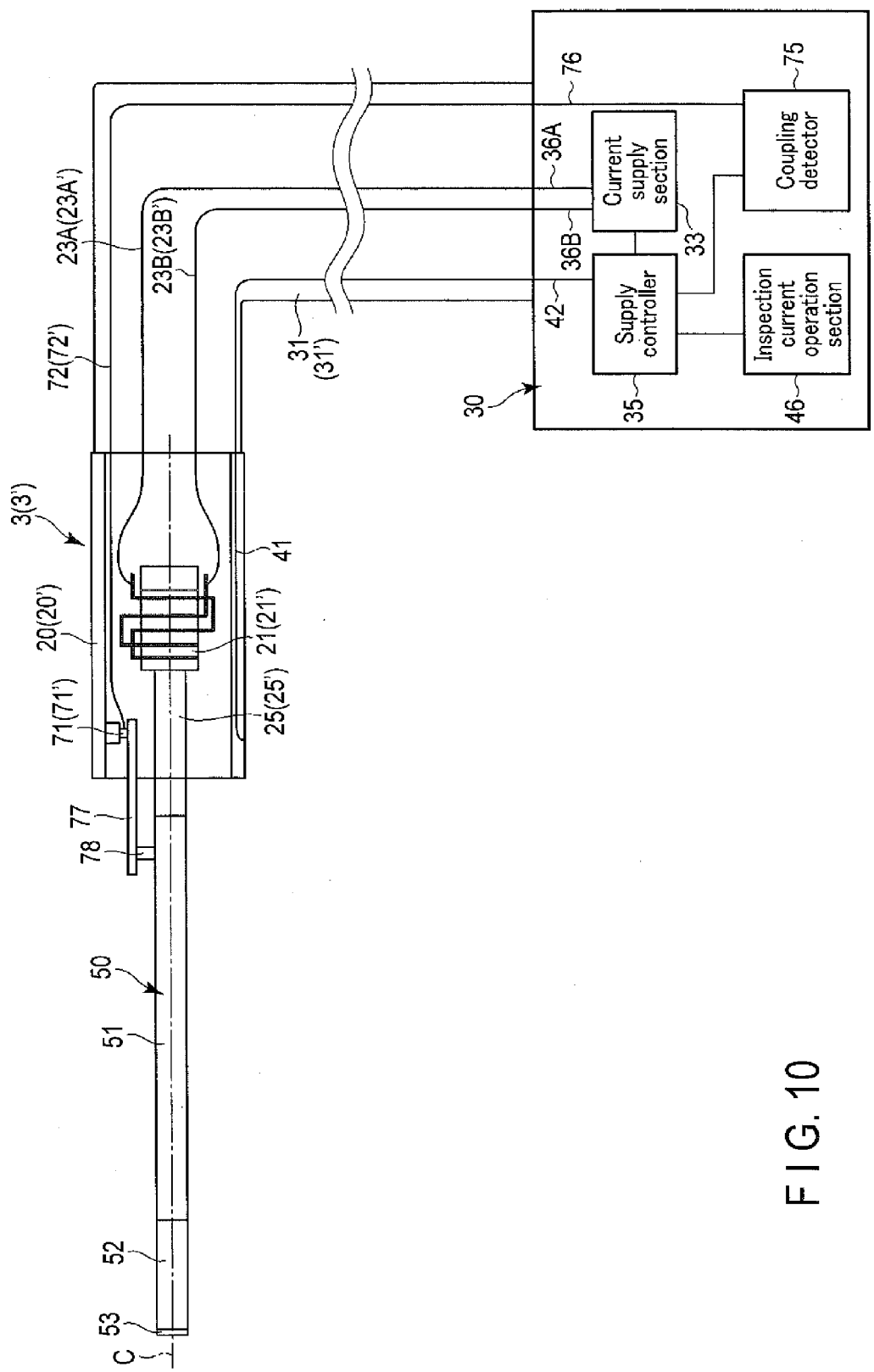
FIG. 10 is a schematic view illustrating an electrical connection state in a state in which an inspection probe according to the second embodiment is coupled to the transducer unit (inspection transducer unit).

FIG. 10 is a view illustrating an electrical connection state in a state in which the inspection probe 50 is connected to the transducer unit 3. In the present embodiment, like the first embodiment, the vibration state by the ultrasonic vibration is inspected in the state in which the inspection probe 50 is coupled to the transducer unit 3. As illustrated in FIG. 10, also in the state in which the inspection probe 50 is coupled to the transducer unit 3, like the case of the treatment time in the ultrasonic treatment apparatus 10, the detection switch 71 and coupling detector 75 are electrically connected via the cable-side signal line 72 and unit-side signal transmitting portion 76.

In the present embodiment, a switch pushing member 77 is attached to the vibration transmission portion 51 of the inspection probe 50. The switch pushing member 77, together with the inspection probe 50, is coupled to the transducer unit 3. An elastic member 78 is provided between the vibration transmission portion 51 and the switch pushing member 77. Thus, no ultrasonic vibration is transmitted from the vibration transmission portion 51 to the switch pushing member 77. In the state in which the inspection probe 50 is coupled to the transducer unit 3, the switch pushing member 77 pushes the detection switch 71 against the urging force. Thereby, the detection switch 71 enters the closed state. By the detection switch 71 entering the closed state, a detection signal is transmitted from the detection switch 71 to the coupling detector 75 via the cable-side signal line 72 and unit-side signal transmitting portion 76. With the detection signal being transmitted, the coupling detector 75 detects the state in which the inspection probe 50 is coupled to the transducer unit 3.

At the time of treatment by the ultrasonic treatment apparatus 10, the detection switch 71 is in the open state, and no detection signal is transmitted to the coupling detector 75. When no detection signal is transmitted to the coupling detector 75, the supply controller 35 controls the current supply section 33 in the treatment mode. Thereby, like the ultrasonic treatment apparatus 10 of the first embodiment, a treatment current (vibration generating current) is supplied from the current supply section 33 to the ultrasonic transducer 21. Then, like the first embodiment, the treated target is treated with use of the ultrasonic vibration.

On the other hand, in the state in which the detection probe 50 is coupled to the transducer unit 3, the detection switch 71 is in the closed state, and a detection signal is transmitted to the coupling detector 75. When the detection signal is transmitted to the coupling detector 75, the supply controller 35 controls the current supply section 33 in the inspection mode. Thereby, like the inspection mode in the first embodiment, the inspection current operation is input in the inspection current operation section 46, and thereby the inspection current is supplied from the current supply section 33 to the ultrasonic transducer 21. In the inspection mode in which the coupling detector 75 has detected the state in which the inspection probe 50 was coupled to the transducer unit 3, the current supply section 33 is controlled in such a state that the current supply section 33 can output an electric current as an inspection current only when the inspection current operation was input. Accordingly, in the inspection mode, the current supply section 33 is controlled in such a state that the current supply section 33 cannot output a current, such as a treatment current, which is other than the inspection current. By the inspection current (current) being supplied to the ultrasonic transducer 21, it is discriminated, like the first embodiment, whether the transducer unit 3 and current control unit 30 are in the normal state in which they are normally actuated (see FIG. 7).

As described above, in the present embodiment, like the first embodiment, the treatment using the ultrasonic vibration is performed and the discrimination of the normal state or otherwise is made, except for the switching between the treatment mode and the inspection mode. Therefore, in the present embodiment, too, it is possible to properly and easily discriminate whether the transducer unit 3 and current control unit 30 are normally actuated or not, by using the inspection probe 50.

In addition, in the present embodiment, by the coupling detector 75 detecting the state in which the inspection probe 50 is coupled to the transducer unit 3, switching is made to the inspection mode. The inspection probe 50 is used by only the inspector who inspects the vibration state, and is not used by the surgeon or the like, who treats the treated target. Thereby, at the time of treatment using the ultrasonic vibration, it is possible to effectively prevent the supply controller 35 from being switched from the treatment mode to the inspection mode.

In the present embodiment, the inspection transducer unit 3' is also provided with a detection switch 71'. Accordingly, the inspection transducer unit 3' has the same structure as the transducer unit 3. Thus, the inspection transducer unit 3' is described with reference to FIG. 10. Incidentally, in FIG. 10, the parts relating to the inspection transducer unit 3' are denoted by reference numerals in parentheses. In addition, in the present embodiment, like the first embodiment, the inspection transducer unit 3' is used only for the inspection of the vibration state by the ultrasonic vibration, and is not used for the treatment by the ultrasonic vibration. Besides, the inspection transducer unit 3' is actuated in the same state as the transducer unit 3 that is normally actuated.

In the inspection transducer unit 3', the detection switch 71' is attached to the inspection transducer case 20'. One end of a cable-side signal line 72' is connected to the detection switch 71'. The cable-side signal line 72' extends through the inside of the inspection transducer case 20' and the inside of the inspection cable 31'. In the detection switch 71', an urging force acts for setting the detection switch 71' in the open state. In addition, the inspection transducer unit 3' is connected to the current control unit 30 via the inspection cable 31', and thereby the cable-side signal line 72' is electrically connected to the unit-side signal transmitting portion 76. Thereby, the detection switch 71' and the coupling detector 75 are electrically connected via the cable-side signal line 72' and the unit-side signal transmitting portion 76.

By the inspection probe 50 being coupled to the inspection transducer unit 3', the switch pushing member 77 pushes the detection switch 71' against the urging force. Thereby, the detection switch 71' enters the closed state. By the detection switch 71' entering the closed state, a detection signal is transmitted from the detection switch 71' to the coupling detector 75 via the cable-side signal line 72' and unit-side signal transmitting portion 76. With the detection signal being transmitted, the coupling detector 75 detects the state in which the inspection probe 50 is coupled to the inspection transducer unit 3'.

With the detection signal being transmitted to the coupling detector 75, the supply controller 35 controls the current supply section 33 in the inspection mode. Thereby, like the first embodiment, the inspection current operation is input in the inspection current operation section 46, and thereby the inspection current is supplied from the current supply section 33 to the inspection ultrasonic transducer 21'. In the inspection mode in which the coupling detector 75 has detected the state in which the inspection probe 50 was coupled to the inspection transducer unit 3', the current supply section 33 is controlled in such a state that the current supply section 33 can output an electric current as an inspection current only when the inspection current operation is input. Accordingly, in the inspection mode, the current supply section 33 is controlled in such a state that the current supply section 33 cannot output a current, such as a treatment current, which is other than the inspection current. By the inspection current (current) being supplied to the inspection ultrasonic transducer 21', the unit (transducer unit 3 or current control unit 30) in which abnormality occurs is specified, as in the first embodiment (see FIG. 8).

As described above, in the present embodiment, like the first embodiment, the unit in which abnormality occurs is specified, except for the switching to the inspection mode. Therefore, in the present embodiment, too, it is possible to properly and easily specify the unit (transducer unit 3 or current control unit 30) in which abnormality occurs, by using the inspection probe 50 and inspection transducer unit 3'.

(Modifications)

In the above-described embodiments, the heat radiation portion 53 is provided as the index section, but the embodiment is not limited to this. For example, as a first modification, as illustrated in FIG. 11, a thermocouple 81 may be provided as the index section on the vibration damping portion 52 of the inspection probe 50. In this modification, the temperature of the thermocouple 81 varies in accordance with a conversion amount from vibration energy to heat energy in the vibration damping portion 52. In addition, with the temperature varying, the electrical resistance value in the thermocouple 81 varies. Specifically, the thermocouple 81 serves as an index indicating the conversion amount to heat energy in the vibration damping portion 52.

In the present modification, a resistance measuring device 82 is provided as a measuring unit. The resistance measuring device 82, which is a resistance measuring section, is electrically connected to the thermocouple 81 via electrical wiring lines 83A and 83B. By supplying a measuring current to the thermocouple 81 through the electrical wiring lines 83A and 83B, the resistance measuring device 82 measures the electrical resistance value of the thermocouple 81 as a physical amount. A measurement result of the measured electrical resistance value of the thermocouple 81 is transmitted to the discrimination section 62 of the discrimination processing unit 60. In addition, the storage section 61 stores a relationship between the inspection current from the current supply section 33 and the electrical resistance value of the thermocouple 81 in the normal state in which the transducer unit 3 is normally actuated. The discrimination section 62 makes a discrimination, based on the measurement result of the electrical resistance value, the information relating to the inspection current, and the relationship in the normal state between the inspection current and the electrical resistance value, which is stored in the storage section 61. If the measured electrical resistance value falls within the predetermined range, it is determined that the transducer unit 3 and the current control unit 30 are in the normal state in which they are normally actuated. On the other hand, if the measured electrical resistance value falls out of the predetermined range, it is determined that abnormality (problem) occurs in the transducer unit 3 or current control unit 30, and the transducer unit 3 or current control unit 30 is not in the normal state.

The unit (transducer unit 3 or current control unit 30) in which abnormality occurs is specified, similarly based on the measured electrical resistance value of the thermocouple 81. At this time, the unit in which abnormality occurs is specified by using the inspection transducer unit 3' in place of the transducer unit 3.

Furthermore, as a second modification, as illustrated in FIG. 12, the discrimination processing unit 60 may not be provided. In this modification, a thermometer 86 is provided as a measuring unit which measures the temperature of the heat radiation portion 53 that is the index section. By putting the thermometer 86 in contact with the heat radiation portion 53, the temperature of the heat radiation portion 53 is measured as a physical amount. The temperature of the heat radiation portion 53 varies in accordance with the conversion amount from vibration energy to heat energy in the vibration damping portion 52.

In the present modification, since the discrimination processing unit 60 is not provided, the inspector, who inspects the vibration state, makes a discrimination of the normal state or otherwise. If the measured temperature is within the predetermined range, the inspector determines that the transducer unit 3 and current control unit 30 are in the normal state in which they are normally actuated. On the other hand, if the measured temperature falls out of the predetermined range, the inspector determines that abnormality (problem) occurs in the transducer unit 3 or current control unit 30, and the transducer unit 3 or current control unit 30 is not in the normal state.

The unit (transducer unit 3 or current control unit 30) in which abnormality occurs is specified, similarly based on the measured temperature of the heat radiation portion 53. At this time, the unit in which abnormality occurs is specified by using the inspection transducer unit 3' in place of the transducer unit 3.

Moreover, as a third modification, as illustrated in FIG. 13, the measuring unit (infrared camera 56 or the like) may not be provided. In the present modification, the inspection probe 50 is provided with a color variation portion 85 as the index section. The color variation portion 85 is, for example, a coating material with a color varying in accordance with temperatures, and is coated on a distal surface of the vibration damping portion 52. The temperature of the color variation portion 85 varies in accordance with the conversion amount from vibration energy to heat energy in the vibration damping portion 52, and the color of the color variation portion 85 varies in accordance with the variation in temperature. Specifically, the color variation portion 85 serves as an index indicating the conversion amount to heat energy in the vibration damping portion 52.

In the present modification, since the discrimination processing unit 60 is not provided, the inspector, who inspects the vibration state, makes a discrimination of the normal state or otherwise. If the color of the color variation portion 85 is a predetermined color (e.g. red), the inspector determines that the transducer unit 3 and current control unit 30 are in the normal state in which they are normally operated. On the other hand, if the color of the color variation section 85 is not the predetermined color, the inspector determines that abnormality (problem) occurs in the transducer unit 3 or current control unit 30, and the transducer unit 3 or current control unit 30 is not in the normal state.

The unit (transducer unit 3 or current control unit 30) in which abnormality occurs is specified, similarly based on the color of the color variation portion 85. At this time, the unit in which abnormality occurs is specified by using the inspection transducer unit 3' in place of the transducer unit 3.

Besides, as a fourth modification, as illustrated in FIG. 14, a cover member 87, which covers the outer peripheral direction side of the inspection probe 50, may be provided. The cover member 87 supports the inspection probe 50 via an elastic member 88. By the provision of the elastic member 88, an ultrasonic vibration is not transmitted to the cover member 87. The cover member 87, together with the inspection probe 50, is coupled to the transducer unit 3. At this time, the cover member 87 is attached to the distal direction side of the transducer case 20. In the state in which the inspection probe 50 is coupled to the transducer unit 3, the vibration damping portion 52 is covered with the cover member 87 over the entire periphery thereof. Thus, the vibration damping portion 52 is not exposed to the outside. Since heat occurs by the conversion from vibration energy to heat energy, the temperature of the vibration damping portion 52 rises to a high level. Since the vibration damping portion 52 with high temperatures is not exposed to the outside, the inspector can inspect the vibration state more safely.

In the meantime, in the above-described embodiments, the handpiece 2, which performs ultrasonic coagulation-and-cutting, was described as an example of the ultrasonic treatment instrument. However, the ultrasonic treatment instrument is not limited to the handpiece 2. For example, in a certain ultrasonic treatment instrument, the jaw (8) is not provided, and the ultrasonic vibration and high-frequency current are transmitted to the treatment section (18) provided in the distal portion of the ultrasonic probe (7). At this time, the treatment section (18) resects a treated target such as a living body tissue by using the supplied high-frequency current, in the state in which the treatment section (18) longitudinally vibrates by the ultrasonic vibration. In addition, in some other ultrasonic treatment instrument, in the state in which a liquid is fed to the treatment section (18) provided in the distal portion of the ultrasonic probe (7), the ultrasonic vibration is transmitted to the treatment section (18) and thereby cavitation occurs near the treatment section (18). At this time, by the cavitation, the treated target such as a living body tissue is crushed and emulsified. In this case, a suction path is provided in the ultrasonic probe (7). The crushed and emulsified treated target is sucked and collected through the suction path of the ultrasonic probe (7).

In the above-described embodiments and modifications, the vibration state by an ultrasonic vibration is inspected by using an inspection probe (50). The inspection probe (50)

includes a vibration transmission portion (51) extends along a longitudinal axis (C), and configured to transmit the ultrasonic vibration from a proximal direction toward a distal direction, and a vibration damping portion (52) continuous with the distal direction side of the vibration transmission portion (51). In the state in which the vibration damping portion (52) vibrates in a manner to follow the vibration transmission portion (51) by the transmission of the ultrasonic vibration from the vibration transmission portion (51), the vibration damping portion (52) causes vibration energy of the ultrasonic vibration to be lost. Then, the vibration damping portion (52) damps the ultrasonic vibration by converting the lost vibration energy to heat energy. The inspection probe (50) further includes an index section (53; 81; 85) to which heat produced by the conversion of the vibration energy to the heat energy in the vibration damping portion (25) is transferred, the index section (53; 81; 85) serving as an index indicating a conversion amount to the heat energy in the vibration damping portion (52).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An inspection probe comprising:
    a vibration transmission portion extends along a longitudinal axis, and configured to transmit an ultrasonic vibration from a proximal direction toward a distal direction;
    a vibration damping portion continuous with a distal direction side of the vibration transmission portion, and configured to damp the ultrasonic vibration by causing vibration energy of the ultrasonic vibration to be lost and converting the lost vibration energy to heat energy in a state in which the vibration damping portion vibrates in a manner to follow the vibration transmission portion by the transmission of the ultrasonic vibration from the vibration transmission portion; and
    an index section to which heat produced by the conversion of the vibration energy to the heat energy in the vibration damping portion is transferred, the index section serving as an index indicating a conversion amount to the heat energy in the vibration damping portion.

2. The inspection probe of claim 1, wherein a boundary position between the vibration transmission portion and the vibration damping portion is located at a position different from an antinode position of the ultrasonic vibration.

3. The inspection probe of claim 1, wherein the vibration damping portion is formed of a damping alloy.

4. A vibration state inspection system comprising:
    the inspection probe of claim 1;
    a transducer unit coupled to a proximal direction side of the inspection probe in a state in which the transducer unit is detachable from the inspection probe, the transducer unit including a vibration generator configured to generate, by being supplied with an inspection current, the ultrasonic vibration which is transmitted to the vibration transmission portion; and
    a current control unit to which the transducer unit is detachably connected, the current control unit including a current supply section configured to supply the inspection current to the vibration generator in a state in which the transducer unit is connected to the current control unit.

5. The vibration state inspection system of claim 4, further comprising a measuring unit configured to measure a physical amount which varies based on the conversion amount to the heat energy in the vibration damping portion, by detecting a variation of the index section based on the conversion amount to the heat energy in the vibration damping portion.

6. The vibration state inspection system of claim 5, further comprising:
    a storage section configured to store a relationship between the inspection current, which is supplied from the current supply section, and the physical amount measured by the measuring unit, in a normal state in which the transducer unit and the current control unit are normally actuated; and
    a discrimination section configured to determine the normal state or otherwise, based on the relationship stored in the storage section between the inspection current and the physical amount in the normal state and a measurement result of the physical amount by the measuring unit.

7. The vibration state inspection system of claim 5,
    wherein the index section includes a heat radiation portion having a temperature varying in accordance with the conversion amount to the heat energy in the vibration damping portion, and having a heat radiation amount varying in accordance with a variation of the temperature, and
    the measuring unit includes a heat measuring section configured to measure the heat radiation amount from the heat radiation portion as the physical amount.

8. The vibration state inspection system of claim 5,
    wherein the index section includes a thermocouple which is attached to the vibration damping portion, and has an electrical resistance value varying in accordance with the conversion amount to the heat energy in the vibration damping portion, and
    the measuring unit includes a resistance measuring section configured to measure the electrical resistance value of the thermocouple as the physical amount, by supplying a measuring current to the thermocouple.

9. The vibration state inspection system of claim 4,
    wherein the index section includes a color variation portion having a temperature varying in accordance with the conversion amount to the heat energy in the vibration damping portion, and having a color varying in accordance with a variation of the temperature.

10. The vibration state inspection system of claim 4, wherein the current control unit includes:
    a coupling detector configured to detect a state in which the inspection probe is coupled to the transducer unit; and
    a supply controller configured to control the current supply section in such a state that the current supply section is capable of outputting the inspection current only when the state in which the inspection probe is coupled to the transducer unit was detected by the coupling detector.

11. The vibration state inspection system of claim 4, wherein the current control unit includes:
    a switching operation section configured to execute a switching operation between a first switching state and a second switching state; and
    a supply controller configured to control the current supply section in such a state that the current supply section is capable of outputting the inspection current only when the switching operation section was changed over to the second switching state.

12. The vibration state inspection system of claim 4, further comprising:
   an inspection transducer unit coupled to the proximal direction side of the inspection probe in a state in which the inspection transducer unit is detachable from the inspection probe, and detachably connected to the current control unit, the inspection transducer unit including an inspection vibration generator configured to generate the ultrasonic vibration by being supplied with the inspection current, the inspection transducer unit being normally actuated in a state in which the inspection current is supplied from the current control unit that is normally actuated,
   wherein the inspection probe is capable of being selectively coupled to either the transducer unit or the inspection transducer unit, and
   either the transducer unit or the inspection transducer unit is selectively connectable to the current control unit.

13. The vibration state inspection system of claim 12, wherein the current control unit includes:
   a coupling detector configured to detect a state in which the inspection probe is coupled to the transducer unit, and a state in which the inspection probe is coupled to the inspection transducer unit; and
   a supply controller configured to control the current supply section in such a state that the current supply section is capable of outputting the inspection current, only when the state in which the inspection probe is coupled to the transducer unit was detected by the coupling detector, and only when the state in which the inspection probe is coupled to the inspection transducer unit was detected by the coupling detector.

14. A method of inspecting a vibration state, comprising:
   supplying an inspection current from a current supply section of a current control unit to a vibration generator of a transducer unit;
   generating an ultrasonic vibration in the vibration generator by the supplied inspection current;
   transmitting the generated ultrasonic vibration from a proximal direction toward a distal direction in a vibration transmission portion provided in an inspection probe which is coupled to a distal direction side of the transducer unit;
   causing vibration energy of the ultrasonic vibration to be lost, and damping the ultrasonic vibration, by transmitting the ultrasonic vibration to a vibration damping portion which is continuous with the distal direction side of the vibration transmission portion, and causing the vibration damping portion to vibrate in a manner to follow the vibration transmission portion;
   converting the lost vibration energy to heat energy in the vibration damping portion, and producing heat;
   transferring the heat, which is produced in the vibration damping portion, to an index section serving as an index indicating a conversion amount to the heat energy in the vibration damping portion, and detecting a variation of the index section to which the heat is transferred; and
   making, based on a relationship between the inspection current, which is supplied from the current supply section, and the variation of the index section in a normal state in which the transducer unit and the current control unit are normally actuated, and based on a detection result of the variation of the index section, a discrimination of the normal state or otherwise.

* * * * *